United States Patent
Minoshima et al.

(10) Patent No.: US 8,472,694 B2
(45) Date of Patent: Jun. 25, 2013

(54) DEVICE FOR GENERATING ALTERNATIVE OF NORMAL BRAIN DATABASE

(75) Inventors: Satoshi Minoshima, Seattle, WA (US); Kiyotaka Watanabe, Tokyo (JP); Shuya Miki, Tokyo (JP); Kazuhiro Nishikawa, Hyogo (JP)

(73) Assignees: University of Washington, Seattle, WA (US); Nihon Medi-Physics Co., Ltd., Tokyo (JP)

(*) Notice: Subject to any disclaimer, the term of this patent is extended or adjusted under 35 U.S.C. 154(b) by 209 days.

(21) Appl. No.: 13/120,053

(22) PCT Filed: Sep. 17, 2009

(86) PCT No.: PCT/JP2009/004692
§ 371 (c)(1),
(2), (4) Date: Jun. 3, 2011

(87) PCT Pub. No.: WO2010/032471
PCT Pub. Date: Mar. 25, 2010

(65) Prior Publication Data
US 2012/0128227 A1    May 24, 2012

(51) Int. Cl.
*G06K 9/00* (2006.01)
(52) U.S. Cl.
USPC .......................................................... 382/134
(58) Field of Classification Search
USPC ....... 382/128–134; 128/920–925; 356/39–49; 600/407–414, 424–426; 345/581–618
See application file for complete search history.

(56) References Cited

U.S. PATENT DOCUMENTS

| | | | |
|---|---|---|---|
| 7,368,098 B2 | 5/2008 | Mueller et al. | |
| 2010/0074480 A1 | 3/2010 | Minoshima et al. | |
| 2010/0080432 A1* | 4/2010 | Lilja et al. | 382/131 |

OTHER PUBLICATIONS

Official Action for U.S. Appl. No. 13/119,914, mailed Feb. 14, 2013.
Chen, et al., "Effect of sample size for normal brain database on diagnostic performance of brain FDG PET for the detection of Alzheimer's disease using automated image analysis", Nuclear Medicine Communications, Mar. 2008, vol. 29, No. 3, pp. 270-276.
Grubbs, "Sample Criteria for Testing Outlying Observations", The annals of Mathematical Statistics, Mar. 1950, vol. 21, No. 1, pp. 27-58.
Maes, et al., "Multimodality Image Registration by Maximization of Mutual Information", IEEE Transactions on Medical Imaging, 1997, vol. 16, No. 2, pp. 187-198.
Minoshima, et al., "Anatomic Standardization: Liner Scaling and Nonlinear Warping of Functional Brain Images", The Journal of Nuclear Medicine, Sep. 1994, vol. 35, No. 9, pp. 1528-1537.

(Continued)

*Primary Examiner* — Atiba O Fitzpatrick
(74) *Attorney, Agent, or Firm* — Jason H. Vick; Sheridan Ross, PC

(57) ABSTRACT

CPU 12 reads out the bloodstream associated values of target voxel of subject's standardized brain bloodstream images (step S34). CPU 12 sorts the bloodstream associated values in descending order (step S35).
CPU 12 rejects bloodstream associated values that are ranked top 10% and bottom 40% (step S36). When the subjects are 20 for example, bloodstream associated values of highest 2 subjects and of lowest 8 subjects are rejected. CPU 12 calculates and stores mean value and standard deviation of remaining bloodstream associated values after the rejection (step S37). CPU 12 calculates mean value and standard deviation of bloodstream associated values for each voxel as target voxel (steps S31, S32, S33 and S38). Then, the alternative normal brain database of brain bloodstream image is obtained.

27 Claims, 27 Drawing Sheets

OTHER PUBLICATIONS

Minoshima, et al., "An Automated Detection of the Intercommissural Line for Stereotactic Localization of Functional Brain Images", The Journal of Nuclear Medicine, Feb. 1993, vol. 34, No. 2, pp. 322-329.

Minoshima, et al., "An Automated Method for Rotational Correction and Centering of Three-Dimensional Functional Brain Images", Journal of Nuclear Medicine, 1992, vol. 33, pp. 1579-1585.

U.S. Appl. No. 13/119,914, filed Mar. 21, 2011, Shuke.

Thompson, "On a Criterion for the Rejection of Observations and the Distribution of the Ratio of Deviation to Sample Standard Deviation", The annals of Mathematical Statistics, Dec. 1935, vol. 6, No. 4, pp. 214-219.

Yamamoto, Y. et al., "The Evaluation of Cerebral Blood Flow SPECT by Statistics Image Analysis (Report from the Scientific Research Group)," Japanese Journal of Radiological Technology, Jun. 20, 2008, vol. 64, No. 6, pp. 752-765 (translation attached) 40 pages.

Matsuo, T. et al., "253 Study on Generating Normal Database for Cerebral Blood Flow SPECT by Statistics Image Analysis (253 nouketuryu SPECT toukeigakuteki kaisekihou ni okeru seijyo detabeisu sakusei ni tsuiteno kento)," Japanese Journal of Radiological Technology, Sep. 20, 2007, vol. 63, No. 9, p. 1049 (translation attached) 6 pages.

International Search Report and Written Opinion for International Patent Application No. PCT/JP2009/004692, mailed Dec. 15, 2009.

Internatioal Preliminary Report on Patentability for International (PCT) Patent Application No. PCT/JP2009/004692, mailed Mar. 31, 2011, 6 pages.

International Search Report for International (PCT) Patent Application No. PCT/JP2009/004693, mailed Dec. 15, 2009, 2 pages.

De Craene et al., "Multi-subject variational registration for probabilistic unbiased atlas generation," IEEE International Conference on Image Processing, Sep. 2005, vol. 3, pp. 601-604.

Passat et al., "Cerebral vascular atlas generation for anatomical knowledge modeling and segmentation purpose," IEEE Computer Society Conference on Computer Vision and Pattern Recognition, Jun. 2005, vol. 2, pp. 331-337.

Schwarz et al., "Comparison of Point Similarity Measures for Atlas-based Registration of MRI Brain Images," Proceedings of the IEEE Engineering in Medicine and Biology Society 27th Annual International Conference, Sep. 2005, pp. 455-458.

English Translation of International Preliminary Report on Patentability for International (PCT) Patent Application No. PCT/JP2009/004693, issued Apr. 19, 2011, 5 pages.

Official Action for U.S. Appl. No. 12/234,910, mailed Aug. 18, 2011, 9 pages.

* cited by examiner

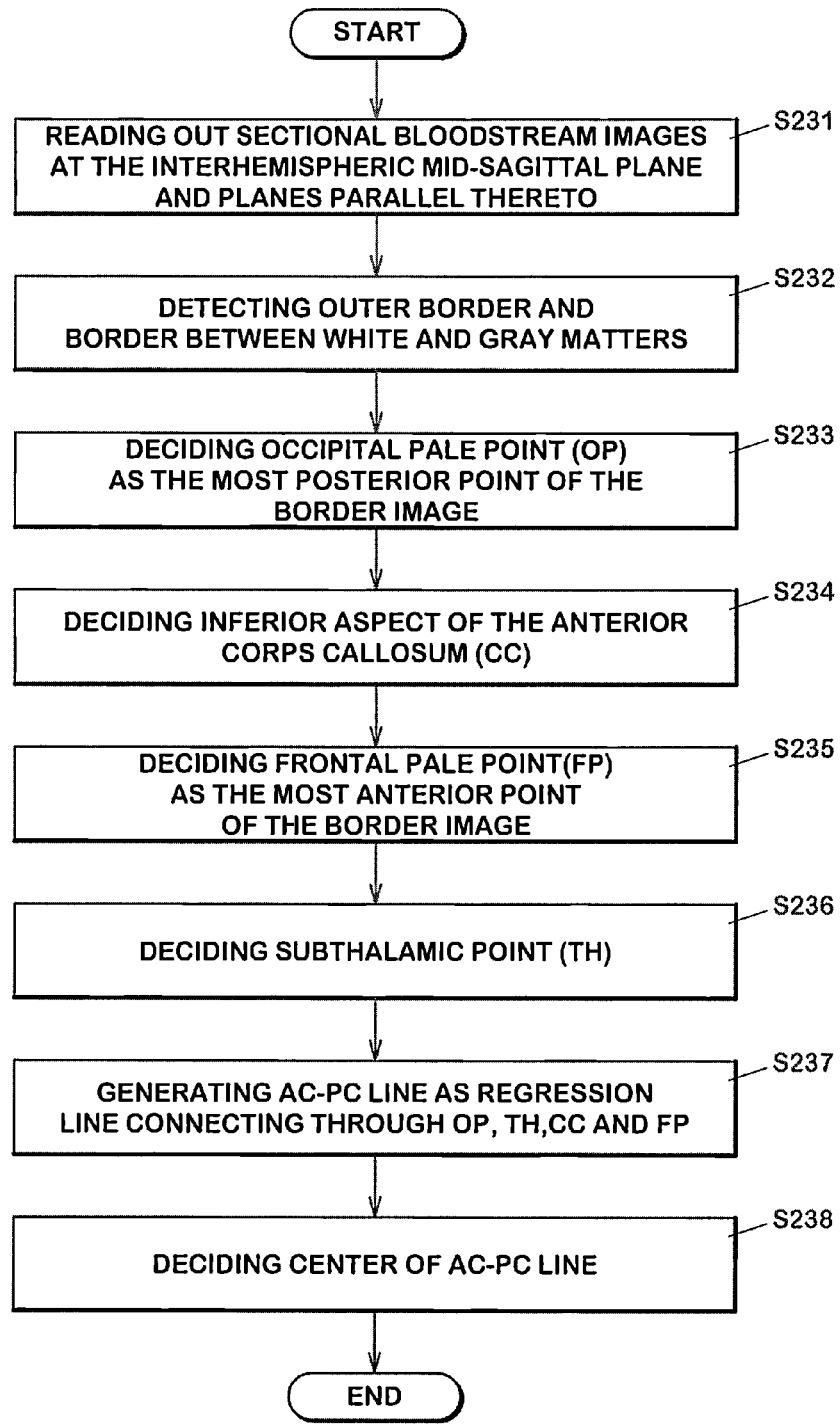

FIG.23

VOXEL (11,25,135)

| SUBJECT ID | BLOODSTREAM ASSOCIATED VALUE |
|---|---|
| 5 | 2.03 |
| 9 | 1.51 |
| 3 | 1.50 |
| 15 | 1.47 |
| ⋮ | ⋮ |
| 4 | 0.22 |
| 10 | 0.20 |
| 2 | 0.13 |

FIG.27

TABLE OF Ta

| M \ RR | 4 | 5 | 6 | 7 | 8 | 9 | 10 | 11 | 12 | 13 | 14 |
|---|---|---|---|---|---|---|---|---|---|---|---|
| 5% | 1.65 | 1.76 | 1.81 | 1.85 | 1.87 | 1.88 | 1.90 | 1.90 | 1.91 | 1.92 | 1.92 |
| 1% | 1.71 | 1.92 | 2.05 | 2.14 | 2.21 | 2.26 | 2.29 | 2.32 | 2.35 | 2.37 | 2.38 |

| M \ RR | 15 | 16 | 17 | 18 | 19 | 20 | 21 | 22 | 23 | 24 | 25 |
|---|---|---|---|---|---|---|---|---|---|---|---|
| 5% | 1.92 | 1.93 | 1.93 | 1.93 | 1.93 | 1.93 | 1.94 | 1.94 | 1.94 | 1.94 | 1.94 |
| 1% | 2.40 | 2.41 | 2.42 | 2.43 | 2.44 | 2.45 | 2.45 | 2.46 | 2.47 | 2.47 | 2.47 |

DEVICE FOR GENERATING ALTERNATIVE OF NORMAL BRAIN DATABASE

CROSS REFERENCE TO RELATED APPLICATIONS

This application is a national stage application under 35 U.S.C. 371 of PCT Application No. PCT/JP2009/004692 having an international filing date of 17 Sep. 2009, which designated the United States, which PCT application claimed the benefit of U.S. application Ser. No. 12/234,910 filed 22 Sep. 2008, each of which are incorporated herein by reference in their entirety.

TECHNICAL FIELD

The present invention relates to generate an alternative of normal brain database (hereinafter referred as "alternative normal brain database") which can be used for diagnosing disease based on functional image of brain such as PET (positron emission tomography) image and SPECT (single photon emission computed tomography) image.

BACKGROUND ART

To diagnose Alzheimer's disease etc., measuring and imaging functional status such as bloodstream or glucose metabolism of each point of patient's brain is carried out. In positron emission tomography (hereinafter referred as "PET"), medical agent which is indicated by positron emission nuclear such as $^{18}$F-FDG is injected to obtain the functional status such as glucose metabolism by measuring gamma ray amount as annihilation radiation at each point of patient's brain. In single photon emission computed tomography (hereinafter referred as "SPECT"), gamma ray emission nuclear species such as $^{123}$I and $^{99m}$Tc is used for the same purpose. As shown in FIG. 1, plural sectional images are generated by measuring gamma ray amount of each section of patient's brain. In the sectional image, for example, red, yellow, green and blue are used for showing areas in descending order of status value such as bloodstream or glucose metabolism associated value (voxel value associating functional value measured by PET of SPECT).

Diagnosis of disease can be carried out by comparing data showing status value of normal healthy subject and data showing status value of patient. For comparing, computer displays differential image between the sectional image of normal healthy subject and the sectional image of patient. To obtain the differential image, the sectional image of patient is spatially fitted to that of normal healthy subject and Z-score at each point is calculated. The method to achieve such diagnosis is well known such as 3-Dimentional stereotaxic surface projection (3D-SSP) developed by Minoshima of Washington University, and Statistical Parametoric Mapping (SPM) developed by Friston et al. of Hammersmith Hospital, U.K.

The data showing status value of normal healthy subject comprises mean and standard deviation of status values of each point which are obtained from plural normal healthy subjects. The data showing status value of normal healthy subject are called as normal brain database. The Z-score is obtained by dividing difference between the status value of patient and the status value of normal healthy subject at each point by standard deviation at each point of normal brain database. See equation (1).

$$Z(x,y,z) = (I_{mean}(x,y,z) - I(x,y,z))/SD(x,y,z) \quad (1)$$

Where $Z(x,y,z)$ is Z-score at the point of coordinate x,y,z, $I_{mean}(x,y,z)$ is mean value of status values (voxel values associated to functional status measured by PET of SPECT etc.) at said point of normal healthy subjects, $I(x,y,z)$ is status value at said point of the patient and $SD(x,y,z)$ is standard deviation of status values at the point of normal healthy subjects. $I_{mean}(x,y,z)$ and $SD(x,y,z)$ can be obtained from the normal brain database.

In this method, difference between normal healthy subject and patient can be clearly shown by using the normal brain database having standard deviation.

In 3D-SSP, the biggest status value from brain surface to predetermined depth perpendicular to the brain surface is selected as representative status value and is displayed on the brain surface. Then, Z-score is calculated by comparing the selected status values of patient with that of normal healthy subjects. Images of Z-score are displayed as right-brain lateral surface RT-LAT, left-brain lateral surface LT-LAT, top surface SUP, bottom surface INF, anterior surface ANT, posterior surface POST, right-brain medial surface R-MED and left-brain medial surface L-MED as shown in FIG. 2. In FIG. 2, upper images (denoted "surface") show status values of brain surface and lower images (denoted "GLB") show Z-score of brain surface. Z-score image enables to improve detection ability of disease and to assess severity of disease.

Mean value and standard deviation of selected status values of brain surface (said selected biggest values) at each point of brain surface of plural normal healthy subjects should be provided as normal brain database in the 3D-SSP method.

To achieve high diagnosing ability, the normal brain database is made based on preferably at least 10 normal healthy subjects. See Chen W P et al., "Effect of sample size for normal brain database on diagnostic performance of brain FDG PET for the detection of Alzheimer's disease using automated image analysis" Nucl Med Commun. 2008 March; 29 (3):270-6.

It is not easy to gather image data of normal healthy subjects, because most of functional brain images such as PET images and SPECT images gathered by the medical center are the functional brain images of subjects who visit medical center and possibly have any disease. Further, functional brain image may vary according to radio isotopes corresponding to disease to be diagnosed and materials indicating them. Therefore, normal brain database should be generated for each combination of radio isotopes and materials indicating them. Above mentioned situations disturb the generation of normal brain database.

CITATION LIST

Non Patent Literature

[NPL 1]
Chen W P et al., "Effect of sample size for normal brain database on diagnostic performance of brain FDG PET for the detection of Alzheimer's disease using automated image analysis" Nucl Med Commun. 2008 March; 29 (3):270-6

SUMMARY OF INVENTION

Technical Problem

In the following description, "brain status image" means image which shows status of brain such as brain functional image.

It is an object of the present invention to provide a device and method which can easily generate alternative of normal brain database which can be used for alternative for the normal brain database which is difficult to generate.

Solution to Problem (1) A device for generating alternative of normal brain database to be used for diagnosing brain disease based on brain status images of subjects including patients, embodying the present invention comprises:

means for normalizing status value at each point of each brain status image of subject based on status values of a part or whole of brain status image of the subject;

means for spatially transforming each brain status image of subject in accordance with anatomical standard brain;

means for rejecting status values presumed as indicating disease with regard to each points of brain to be used for diagnosing disease based on said anatomically transformed and normalized brain status images of subjects; and means for generating the alternative of normal brain database by obtaining at least mean status value for said each point of brain to be used for diagnosing disease based on said anatomically transformed and normalized brain status images of subjects in which said status values presumed as indicating disease are rejected.

(2) In one embodiment of the present invention, the rejecting means rejects extreme deviate values statistically obtained at each point as said status values presumed as indicating disease.

(3) In one embodiment of the present invention, the brain status image is a brain bloodstream image which shows bloodstream associated value (voxel value obtained by PET or SPECT etc. associated with the bloodstream value) of each points of brain.

(4) In one embodiment of the present invention, the rejecting means rejects the smallest value to the m-th smallest as said status values presumed as indicating disease for each points of brain to be used for diagnosing disease based on anatomically transformed and normalized brain status images of subjects.

(5) In one embodiment of the present invention, the rejecting means further rejects the largest value to the n-th largest for each points of brain to be used for diagnosing disease based on anatomically transformed and normalized brain status images of subjects.

(6) In one embodiment of the present invention, the number m of rejecting the smallest value to the m-th smallest is larger than the number n of rejecting the largest value to the n-th largest.

(7) In one embodiment of the present invention, the generating means generates the alternative of normal brain database by obtaining mean status value and standard deviation for said each point of brain to be used for diagnosing disease based on said anatomically transformed and normalized brain status images of subjects in which said status values presumed as indicating disease are rejected.

(8) A device for generating alternative of normal brain database embodying the present invention further comprises:

means for generating brain surface status image of each subjects based on said anatomically transformed and normalized brain status images of subjects, said brain surface status image having surface status value of each surface portions, said surface status value being selected as representative value of status values from brain surface to predetermined depth perpendicular to the brain surface; and wherein said each surface point at which said surface status value is indicated is used as said point of brain to be used for diagnosing disease.

Brain surface bloodstream image or brain surface glucose metabolism image as the brain surface status image can be generated by bloodstream values of brain bloodstream image or glucose metabolisms of brain glucose metabolism image, respectively.

(9) A device for generating alternative of normal brain surface database to be used for diagnosing disease, based on brain bloodstream images of subjects including patients which show bloodstream associated value of each points of brain, embodying the present invention comprises:

means for normalizing bloodstream associated value at each point of each brain bloodstream image of subject based on bloodstream associated values of a part or whole of brain bloodstream image of the subject;

means for spatially transforming each brain bloodstream image of subject in accordance with anatomical standard brain;

means for generating brain surface bloodstream image of each subjects based on said anatomically transformed and normalized brain bloodstream images of subjects, said brain surface bloodstream image having surface bloodstream associated value of each surface points, said surface bloodstream associated value being selected as representative value of bloodstream associated values from brain surface to predetermined depth perpendicular to the brain surface; and means for generating the alternative of normal brain surface bloodstream database by obtaining mean bloodstream associated value and standard deviation for each surface points based on generated brain surface bloodstream image of each subjects, said mean bloodstream associated value and standard deviation being obtained by calculating average of selected bloodstream associated values and standard deviations of the surface portion, said selected bloodstream associated values are selected from all bloodstream associated values of the surface portion by excluding at least the smallest value to the m-th smallest.

The forgoing forms and other forms, objects, and aspects as well as features and advantages of the present invention will become further apparent from the following detailed description of the presently preferred embodiments, read in conjunction with the accompanying drawings. The detailed description and drawings are merely illustrative of the present invention rather than limiting the scope of the present invention being defined by the appended claims and equivalents thereof.

BRIEF DESCRIPTION OF DRAWINGS

FIG. 15 is a detailed flowchart for identifying the AC-PC line and the center thereof (step S23 of FIG. 10).

FIG. 23 shows a temporally table for rejecting bloodstream associated value (s) presumed as indicating disease with regard to particular voxel.

FIG. 27 shows a table of T for rejecting in another embodiment.

DESCRIPTION OF EMBODIMENTS

1. Functional Block Diagram

Figure 3:
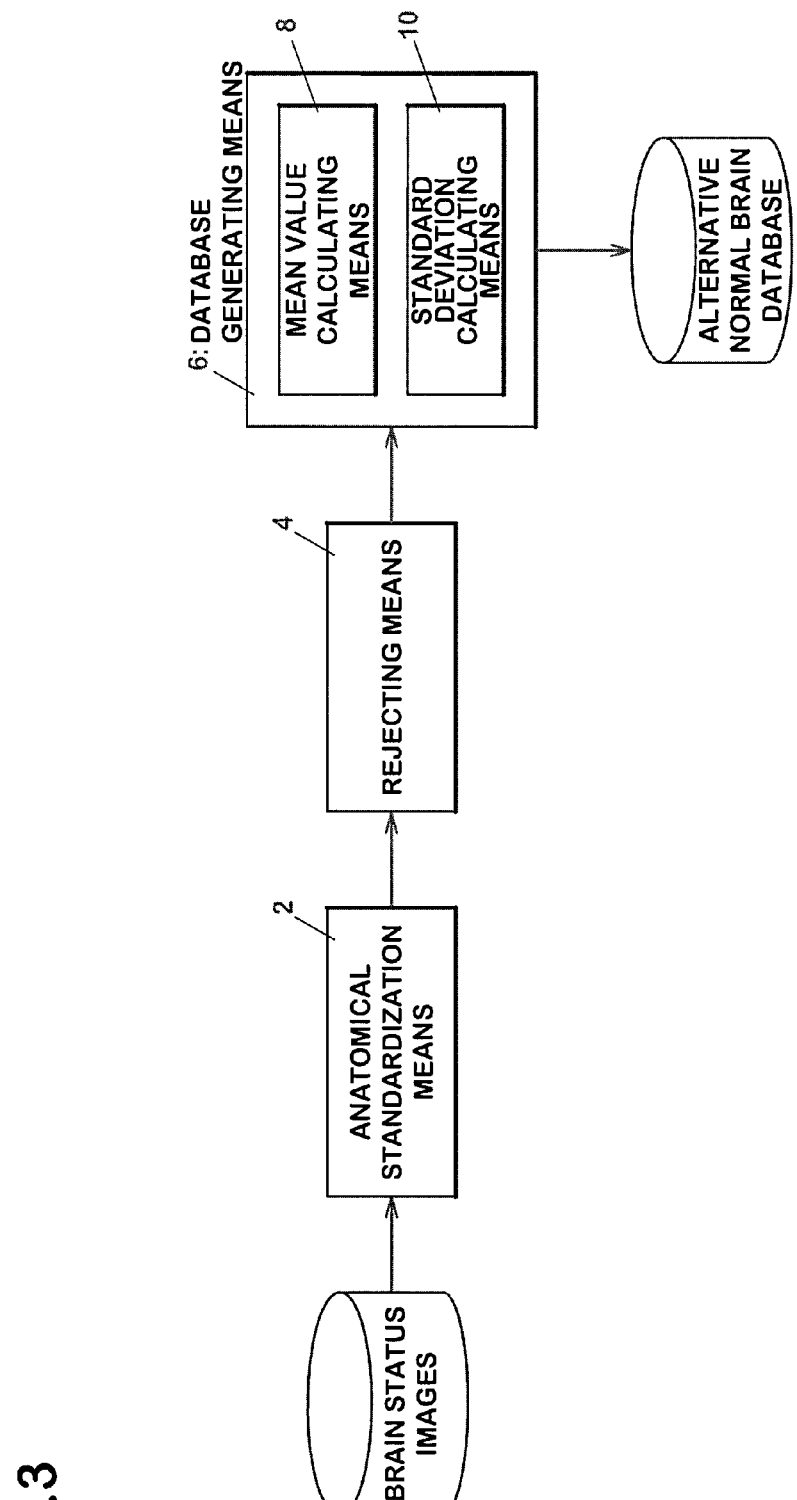
FIG. 3 shows a block diagram of a device for generating alternative of normal brain database (hereinafter referred to as "alternative normal brain database").

FIG. 3 shows a functional block diagram of a device for generating alternative normal brain database of an embodiment of the present invention. The device is adapted to be able to generate the alternative normal brain database based on plural brain status images of subjects including patient(s). All of the plural brain status images provided to the device may be patient's brain status images.

Referring to FIG. 3, anatomical standardization means 2 obtains the brain status images having brain status values and spatially transforms the brain status image of each subject in accordance with anatomical standard brain such as Talairach's standard brain so that the brain status image of each subject is standardized by adjusting spatial differences.

Rejecting means 4 identifies the brain status values presumed as indicating disease based on a comparison of the brain status values of subjects with each other at each point of the standardized brain images. Then the rejecting means 4 rejects the brain status values presumed as indicating disease. This rejecting process may be carried out based on statistical method. In one embodiment, the brain status values of each point are sorted in descending order and the n-th largest and/or the m-th smallest values are rejected. The rejecting means 4 carries out the rejecting process for all of the points.

Database generating means 6 comprises mean value calculating means 8 and standard deviation calculating means 10. The mean value calculating means 8 calculates mean value of remaining brain status values after rejecting process with regard to each point. The standard deviation calculating means 10 calculates standard deviation of remaining brain status values after rejecting process with regard to each point. The calculated mean value and standard deviation is recorded associated with the information showing the position of each point. The mean values, standard deviations and positions constitute the alternative normal brain database.

Figure 4:
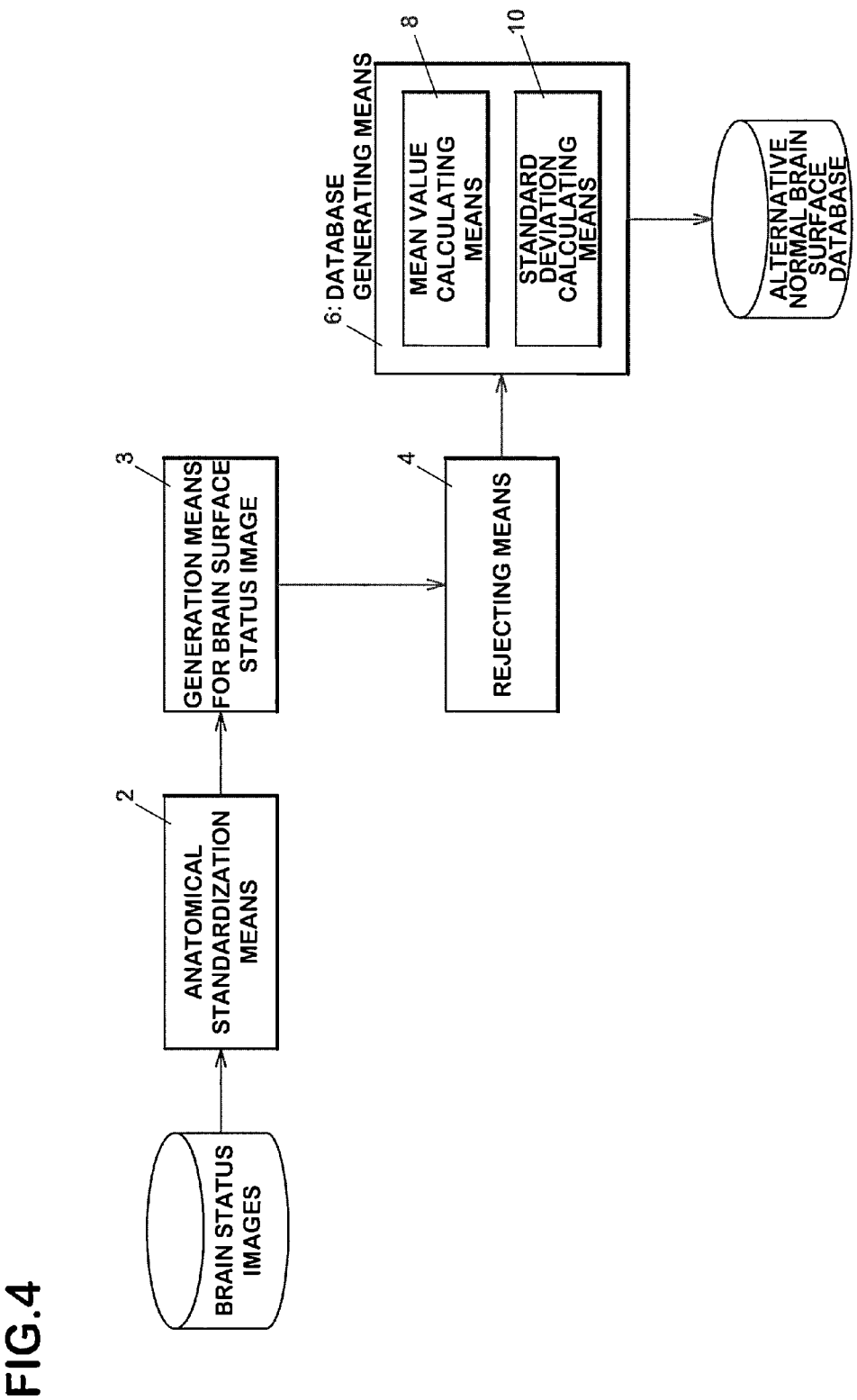
FIG. 4 shows a block diagram of a device for generating alternative normal brain database in another embodiment of the present invention.

FIG. 4 shows a functional block diagram of a device for generating alternative normal brain database in another embodiment of the present invention. The device generates alternative normal brain database of brain surface status for such as Three-Dimensional Stereotactic Surface Projection (3D-SSP) method.

Referring to FIG. 4, anatomical standardization means 2 obtains the brain status images having brain status values and spatially transforms the brain status image of each subject in accordance with anatomical standard brain.

Generating means 3 generates brain surface status image that has representative status value of each point of the brain surface which are selected from status values near the brain surface. The generating means 3 generates the brain surface status images of all subjects.

Rejecting means 4 rejects the brain surface status values presumed as indicating disease by comparing the brain surface status values of all subjects with each other at each point of the standardized brain status images.

Database generating means 6 comprises mean value calculating means 8 and standard deviation calculating means 10. The mean value calculating means 8 calculates mean value of remaining brain surface status values after rejecting process with regard to each point. The standard deviation calculating means 10 calculates standard deviation of remaining brain surface status values after rejecting process with regard to each point. The each calculated mean value and standard deviation is recorded at each point of the standardized brain status images. The mean values, standard deviations and positions are comprised of the alternative normal brain database.

2. Hardware Construction

Figure 5:
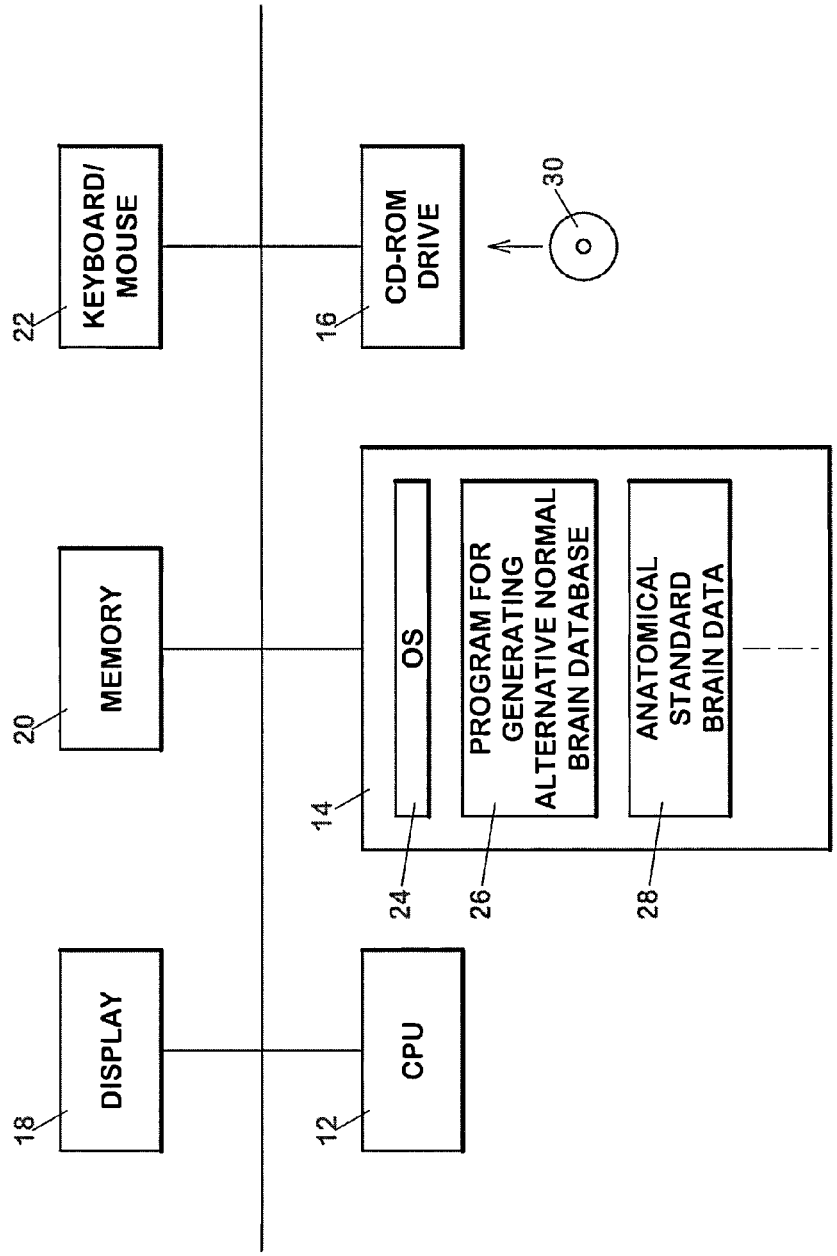
FIG. 5 shows a hardware construction of the device for generating alternative normal brain database.

FIG. 5 shows hardware construction of the device of FIGS. 3 and 4. Although the device realizes both the functions shown in FIGS. 3 and 4 in the following embodiment, the device may have either function. In the following embodiment, brain bloodstream associated value is disclosed as an example of brain status value.

CPU 12 is connected to hard-disk drive 14, CD-ROM drive 16, display device 18 for displaying brain image etc., memory 20 and keyboard/mouse 22. The memory 20 is used for working area of CPU 12. Keyboard/mouse 22 is for inputting instructions from user.

The hard-disk records operating system (OS) 24 such as WINDOWS™, generating program 26 for alternative normal brain database and anatomical standard brain data 28. These programs and data are installed from recording medium such as CD-ROM 30 by using CD-ROM drive 16. The generating program 26 fulfills its function by cooperating with the OS 24.

3. Process by the Generating Program 26 for Normal Database

Figure 6:
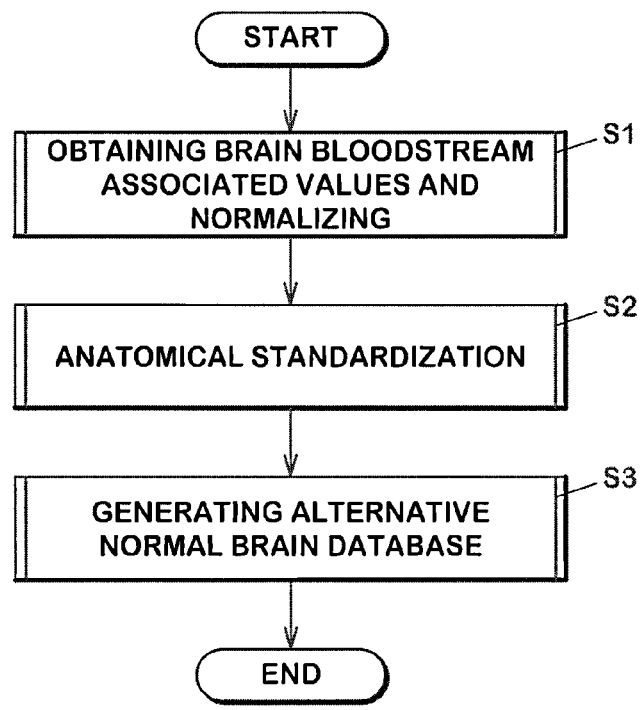
FIG. 6 is a flowchart of the program for generating alternative normal brain database stored in hard-disk.

FIG. 6 is a flowchart of the generating program for alternative normal brain database. The generating process comprises three steps, obtaining brain bloodstream associated values and normalizing (step S1), anatomical standardization (step S2) and generating alternative normal brain database (step S3). Although brain bloodstream associated value is used in the following embodiment, other functional image (value) may be used.

3.1 Obtaining Brain Bloodstream Associated Values and Normalizing (Step S1)

Figure 7:
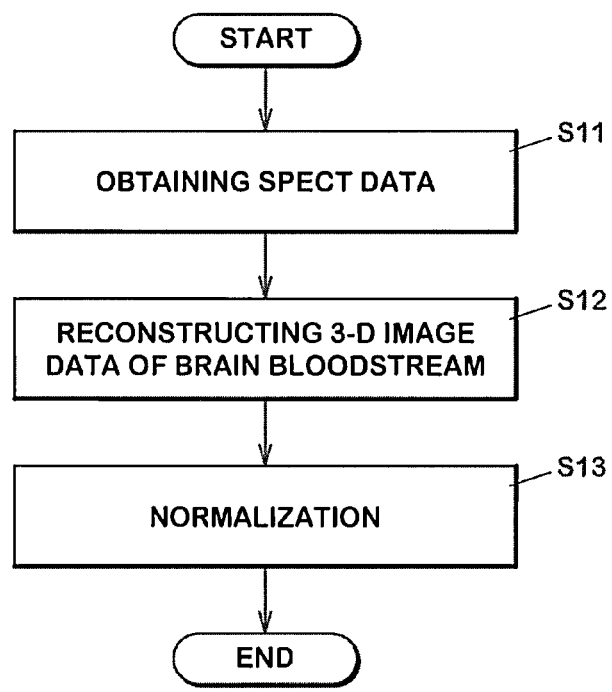
FIG. 7 is a detailed flowchart for obtaining brain bloodstream data (step S1 of FIG. 6)

Detailed steps for obtaining and normalizing brain bloodstream associated values are shown in FIG. 7. First, CPU 12 obtains SPECT data of plural subjects including patient(s) (step S11). The device shown in FIG. 5 can obtain the SPECT data directly from SPECT device when the device is connected to SPECT device through local area network (LAN) etc. The device may obtain the SPECT data by reading the data from recording medium on which SPECT device records measured data (SPECT data). The SPECT data comprises projection data obtained from the subject by using SPECT device.

CPU 12 reconstructs three-dimensional image data which has bloodstream associated values of, for example, 2 mm cubic vowels based on the SPECT data (step S12).

Then, CPU 12 normalizes the voxel values, because the voxel value of the three-dimensional image comes under the influence of measurement condition differences including measurement device difference. In the normalizing step, CPU 12 divides the bloodstream associated value of each point, i.e. each voxel, by mean value of bloodstream associated values of entire each subject's brain (mean value of entire brain voxels) and records the divided value as normalized bloodstream associated value on the hard-disk 14.

Mean value of bloodstream associated values of subthalamic, cerebella, pons or sensorimotor cortex may be used as normalizing standard part instead of the mean value of bloodstream associated values of entire brain in normalizing step. Subthalamic, cerebella, pons or sensorimotor cortex from the SPECT data can be identified by superposing the subject's image on the anatomical standard brain image in which area of each part is predetermined. The normalizing standard part is suitably a part where reduction of bloodstream associated value is not observed in the disease to be diagnosed.

Figure 8:
FIG. 8 shows normalized brain bloodstream data.
Figure 9:
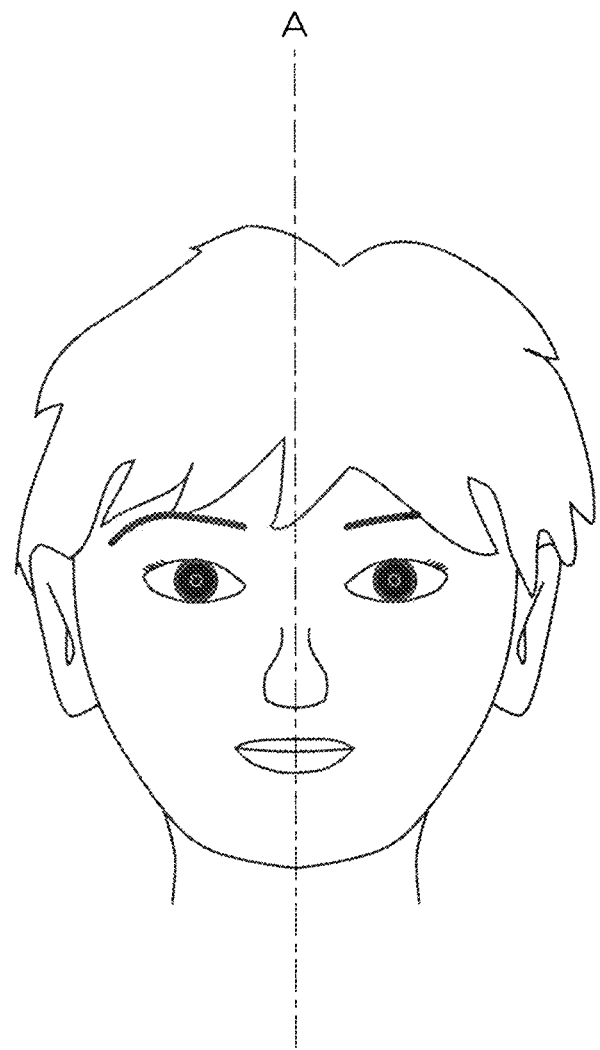
FIG. 9 shows X axis, Y axis and Z-axis relating to cephalon.

FIG. 8 shows normalized data of three-dimensional bloodstream image. In FIG. 8, column "X, Y, Z" represents position data in three-dimensional coordinate, X indicates X-coordinate data, Y indicates Y-coordinate data and Z indicates Z-coordinate data. As shown in FIG. 9, X denotes horizontal direction, Y denotes anteroposterior direction and Z denotes up and down direction of head. The normalized bloodstream data are generated for each subject and recorded on hard-disk 14.

3.2 Anatomical Standardization (Step S2)

Figure 10:
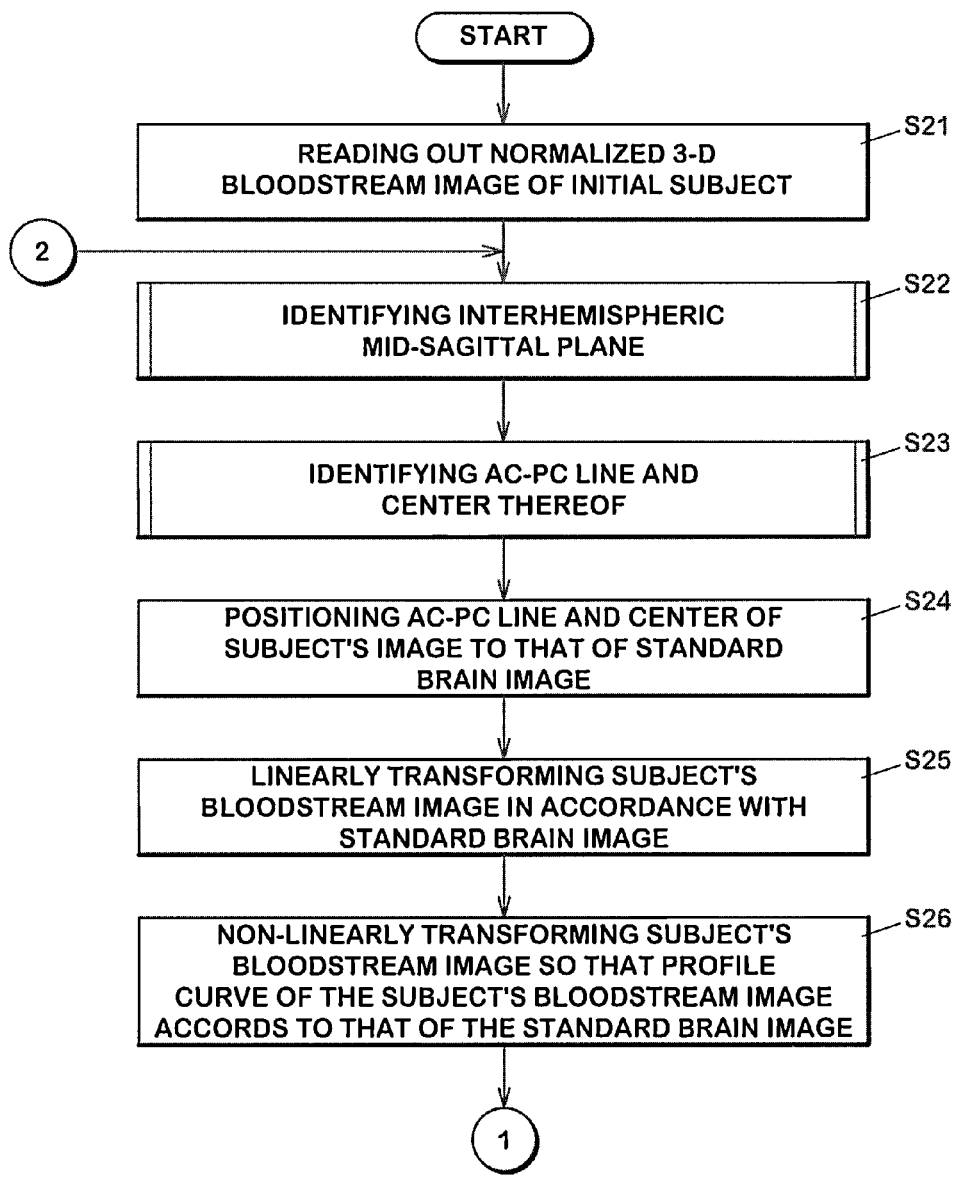
FIG. 10 shows a detailed flowchart for standardizing the bloodstream image (step S2 of FIG. 6).
Figure 11:
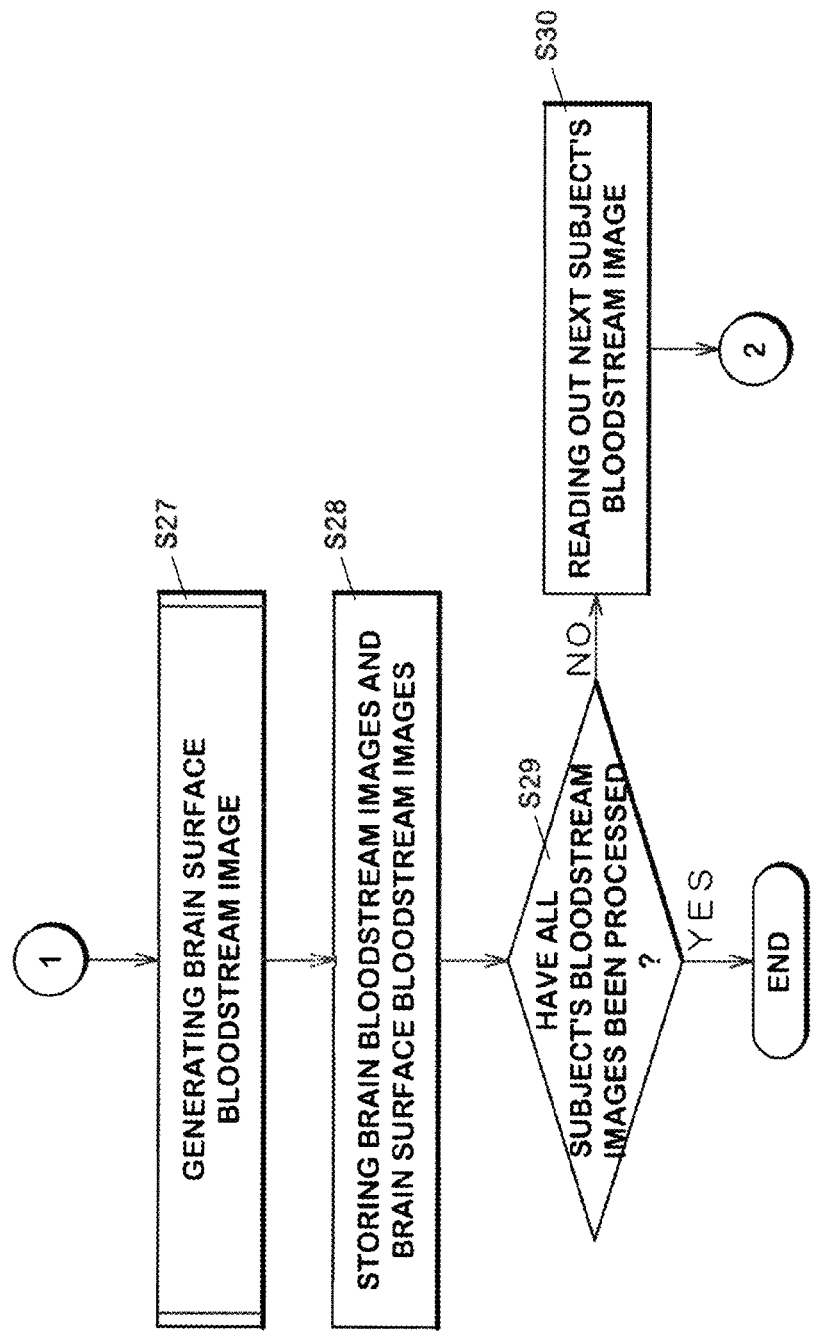
FIG. 11 shows a detailed flowchart for standardizing the bloodstream image (step S2 of FIG. 6).

CPU 12 spatially transforms normalized three-dimensional bloodstream image of each subject in accordance with anatomically standard brain (step S2 of FIG. 6). Detailed flowchart of anatomical standardization is shown in FIGS. 10 and 11.

3.2.1 Identifying the Interhemispheric Mid-Sagittal Plane

CPU 12 reads out the normalized 3-D bloodstream image (see FIG. 8) of initial subject from the hard-disk 14 (step S21). Then, CPU 12 identifies the interhemispheric mid-sagittal plane of the normalized 3-D bloodstream image read out in step S21 (step S22). Referring to FIG. 9, the interhemispheric mid-sagittal plane is defined as Y-Z plane including line A which passes center of a head in a horizontal direction: that is, a plane which equally divides the head with regard to horizontal direction.

In this embodiment, briefly, method for identifying the interhemispheric mid-sagittal plane is as follows:

First, center point of the normalized 3-D bloodstream image is identified and a Y-Z plane including the center point is assumed as the interhemispheric mid-sagittal plane. Then, the normalized 3-D bloodstream image is flipped with respect to the assumed interhemispheric mid-sagittal plane as flipping plane. An image which is symmetric to the assumed interhemispheric mid-sagittal plane is generated. Similarity index between the generated plane symmetry image and original image (the normalized 3-D bloodstream image) is calculated.

Then, the assumed interhemispheric mid-sagittal plane is moved along the X direction, rotated around the Z axis and rotated around the Y axis. The similarity index is calculated for each assumed interhemispheric mid-sagittal plane.

The interhemispheric mid-sagittal plane is identified by selecting the assumed interhemispheric mid-sagittal plane which has maximum similarity index, because the similarity index should be maximum when the normalized 3-D bloodstream image is flipped at center plane.

Figure 12:
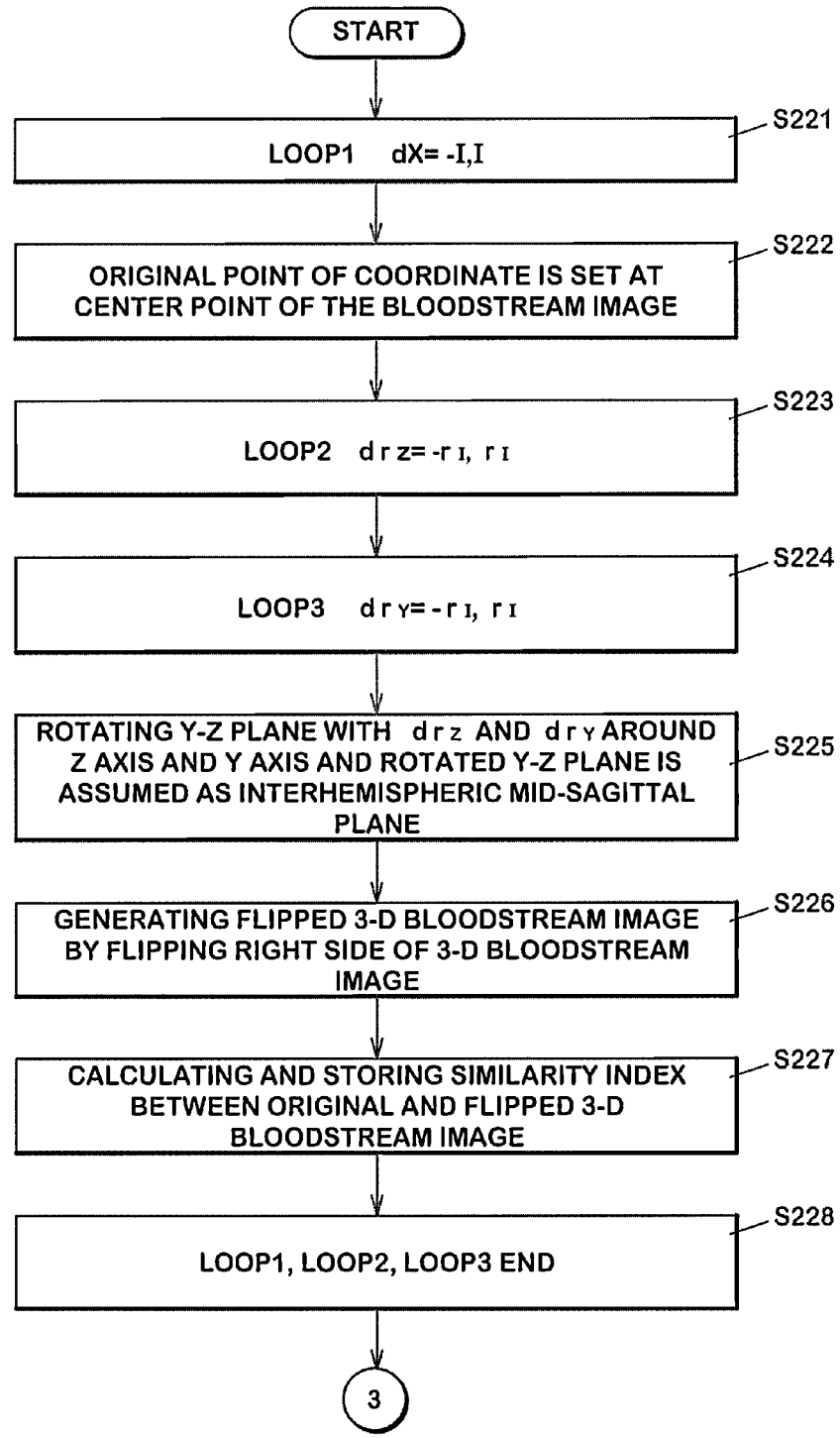
FIG. 12 shows a detailed flowchart for identifying the interhemispheric mid-sagittal plane of the bloodstream image (step S22 of FIG. 10).
Figure 13:
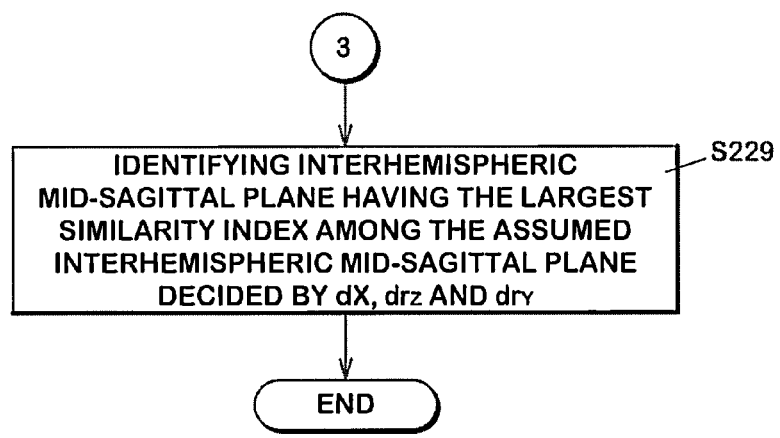
FIG. 13 shows a detailed flowchart for identifying the interhemispheric mid-sagittal plane of the bloodstream image (step S22 of FIG. 10).

Detailed flowchart for identifying the interhemispheric mid-sagittal plane is shown in FIGS. 12 and 13. CPU 12 decides center point $x_0$, $y_0$, $z_0$ of the normalized 3-D bloodstream image by simply using coordinate position. New center point is determined by moving the center point along X direction with dx (step S222).

CPU 12 assumes that original point of coordinate is as the new center point and rotates the Y-Z plane which passes through the center point around the Z axis with drz and around the Y axis with dry. CPU 12 assumes the moved and rotated plane as the interhemispheric mid-sagittal plane (step S225)

CPU 12 generates flipped normalized 3-D bloodstream image which is symmetric to the assumed interhemispheric mid-sagittal plane by flipping the normalized 3-D bloodstream image (step S226). Then, CPU 12 calculates similarity index between the original and the flipped normalized 3-D bloodstream images (step S227). In this embodiment, Stochastic Sign Change (SSC) is calculated as similarity index.

Concept of calculating SSC is as follows:

Consider two similar but not identical images $I_1(x, y)$ and $I_2(x, y)$, where $I(x, y)$ is the pixel count and x, y=1, 2, ... n are the coordinates of the digitized images. Let $S(x, y)=I_1(x, y)-I_2(x, y)$ be the subtraction image. If $I_1(x, y)$ and $I_2(x, y)$ contain additive noise which can be assumed to have a zero mean with a symmetric density function, each pixel value of $S(x, y)$ is not zero but shows random fluctuations around zero, either positive or negative values with equal probability. If there is a dissimilar part of the images between $I_1(x, y)$ and $I_2(x, y)$, the pixel values of $S(x, y)$ in that part will no longer exhibit random fluctuations and will show groupings of all positive or negative values. Let SSC represent the number of sign changes in a sequence of the $S(x, y)$, scanned line-by-line or column-by-column. Accordingly, SSC shows a lager number of sign changes when $I_1(x, y)$ and $I_2(x, y)$ are similar and a lower value when $I_1(x, y)$ and $I_2(x, y)$ are dissimilar. Therefore, the SSC criterion can be defined as a similarity criterion between two images. This concept can be applied on judging the similarity between two three-dimensional images.

Figure 14:
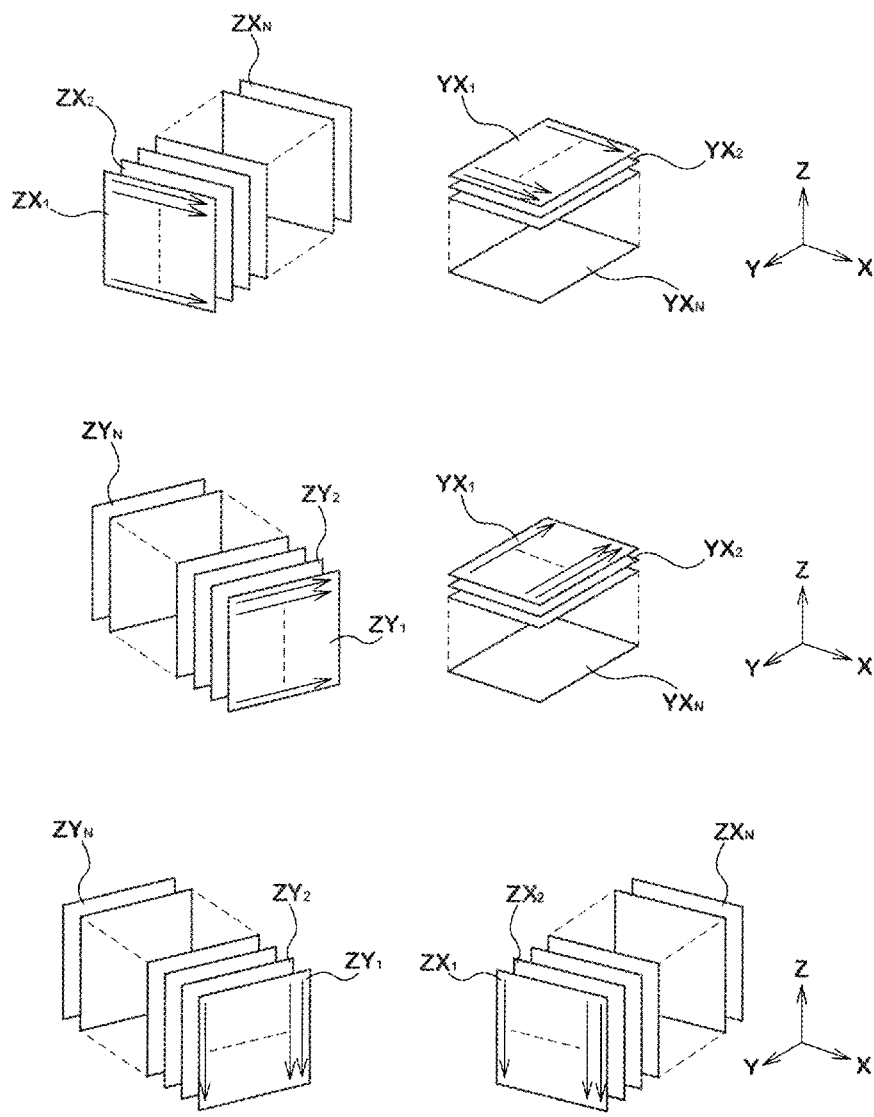
FIG. 14 shows calculation of the stochastic sign change (SSC).

SSC is calculated by summation of $SSC_x$, $SSC_y$ and $SSC_z$ in this embodiment. Referring to FIG. 14, planes $ZX_1$, $ZX_2$, ... $ZX_N$ and planes $YX_1$, $YX_2$, ... $YX_N$ are assumed for calculating $SSC_x$. For each plane, SSC is calculated by scanning the plane. $SSC_x$ is calculated by summation of SSC of all planes $ZX_1$, $ZX_2$, ... $ZX_N$ and $YX_1$, $YX_2$, ... $YX_N$. CPU 12 also calculates $SSC_y$ by summation of SSC of planes $ZY_1$, $ZY_2$, ... $ZY_N$ and planes $YX_1$, $YX_2$, ... $YX_N$ and $SSC_z$ by summation of SSC of planes $ZY_1, ZY_2, \ldots ZY_N$ and planes $ZX_1, ZX_2, \ldots ZX_N$. Then, CPU 12 obtains SSC(dx, drz, dry) with regard to the assumed interhemispheric mid-sagittal plane as summation of $SSC_x$, $SSC_y$ and $SSC_z$ and stores SSC (dx, drz, dry) on the memory 20.

CPU 12 changes dx from −I to I at 1 voxel step to move the assumed interhemispheric mid-sagittal plane along X axis and changes drz and dry from −rI to rI to rotate the assumed interhemispheric mid-sagittal plane. CPU 12 calculates SSC (dx, drz, dry) for all assumed interhemispheric mid-sagittal planes which are determined by all combinations of dx, drz and dry (step S221, S223 and S224).

After calculating SSC(dx, drz, dry) of all the assumed interhemispheric mid-sagittal planes, CPU 12 identifies the interhemispheric mid-sagittal plane which has the largest SSC(dx, drz, dry) among all the assumed interhemispheric mid-sagittal planes (step S229). Identifying the interhemispheric mid-sagittal plane is disclosed in Minoshima et al., "An Automated Method for Rotational Correction and Centering of Three-Dimensional Functional Brain Images" J Nucl Med 1992; 33: 1579-1585, which is expressly incorporated by reference herein.

3.2.2 Identifying AC-PC Line and the Center Thereof

After identifying the interhemispheric mid-sagittal plane, CPU 12 identifies line which passes through the anterior and the posterior commissures of the brain (herein after referred to as "AC-PC line") and the center thereof (step S23 of FIG. 10). In this embodiment, 4 landmarks, occipital pole point (OP), the subthalamic point (TH), the inferior aspect of the anterior corps callosum (CC) and the frontal pole point (FP) of the brain are decided and then AC-PC line is identified as straight line connecting the 4 landmarks.

Figure 16A:
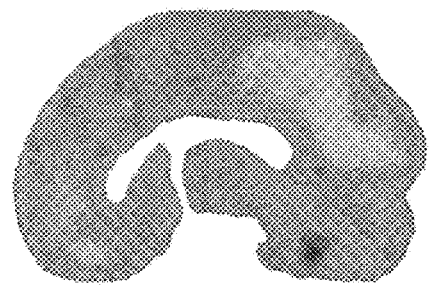
FIG. 16 shows steps for identifying the AC-PC line.

Detailed flowchart for identifying AC-PC line and center thereof is shown in FIG. 15. CPU 12 reads out sectional bloodstream image at the interhemispheric mid-sagittal plane from the hard-disk 14. CPU 12 further reads out sectional bloodstream images of planes which are parallel to and near the interhemispheric mid-sagittal plane (step S231). FIG. 16A shows an example of the sectional bloodstream image at the interhemispheric mid-sagittal plane.

Figure 16B:
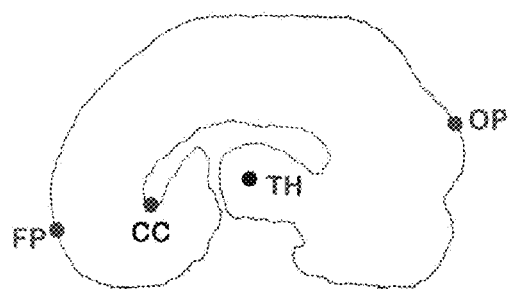

CPU 12 detects outer border of brain and border between white matter and gray matter of brain for each normalized 3-D bloodstream image (step S232). The detection can be carried out by detecting the border between the area of bloodstream existing and the area of bloodstream non-existing. FIG. 16B shows detected border image of the interhemispheric mid-sagittal plane for example.

Then, CPU 12 identifies the occipital pole point (OP) as the most posterior point of the border image of the interhemispheric mid-sagittal plane (see FIG. 16B). CPU 12 also identifies the occipital pole points (OPs) for the other border images of the other sectional bloodstream images. CPU 12 calculates mean of y coordinate values and mean of z coordinate values of all the identified occipital pole points (OPs). CPU 12 decides the position of the occipital pole point (OP) based on the mean of y coordinates values and mean of z coordinate values on the interhemispheric mid-sagittal plane (step S233).

Figure 16C:

Next, CPU 12 finds out U shaped border area as shown in FIG. 16C. The inferior aspect of the anterior corps callosum (CC) is decided by detecting contact point of U shaped border and tangent line from the occipital pole point (OP) to the U shaped border based on the border image. CPU 12 decides the inferior aspect of the anterior corps callosum (CC) for each border image of the sectional bloodstream image. CPU 12 calculates mean of y coordinate values and mean of z coordinate values of all the found inferior aspect of the anterior corps callosum (CC). CPU 12 decides the position of the inferior aspect of the anterior corps callosum (CC) based on the mean of y coordinate values and mean of z coordinate values on the interhemispheric mid-sagittal plane (step S234).

CPU 12 identifies the frontal pole point (FP) as the most anterior point of the border image of the interhemispheric mid-sagittal plane (see FIG. 16B). CPU 12 also identifies the frontal pole points (FPs) based on the other border images of the other sectional bloodstream images. CPU 12 calculates mean of y coordinate values and mean of z coordinate values of all the identified frontal pole points (FPs). CPU 12 decides the position of the frontal pole point (FP) based on the mean of y coordinate values and mean of z coordinate values on the interhemispheric mid-sagittal plane (step S235).

CPU 12 decides the subthalamic point (TH) (step S236). To decide the subthalamic point (TH), CPU 12 finds out the thalamic center at first. The thalamic center can be estimated as the point having local maximum bloodstream associated value and near the AC-PC line. In this embodiment, CPU 12 finds out a point having the local maximum bloodstream associated value within the circle of radius r on the sectional bloodstream image and identifies the point as the thalamic center, where center of the circle is a center point of line connecting the occipital pole point (OP) and the frontal pole point (FP) and the radius r is tenth of the length between OP and FP.

Figure 17A:
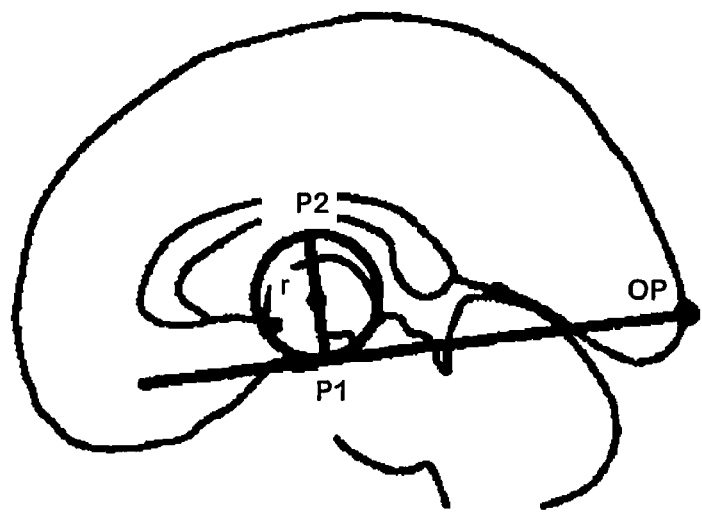
FIG. 17 shows estimating the landmark TH for identifying the AC-PC line.
Figure 17B:
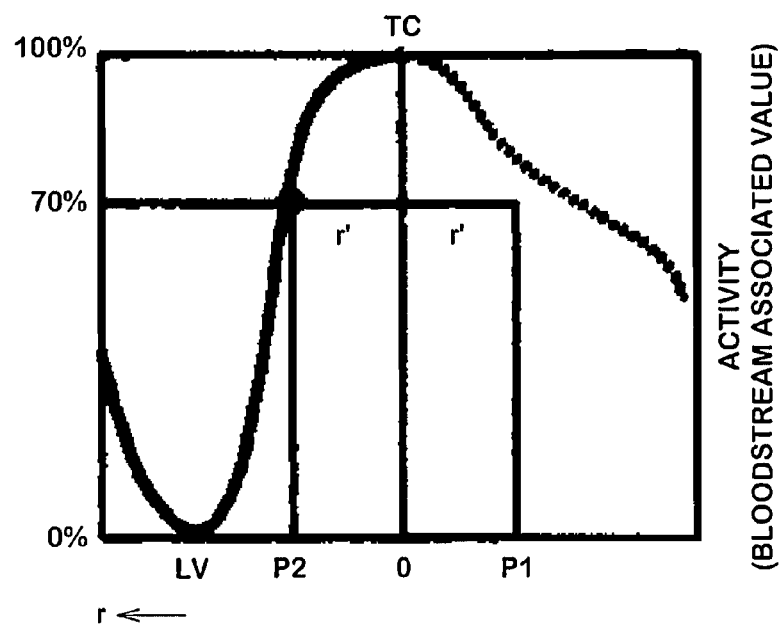

After deciding the thalamic center, CPU 12 plots an imaginary circle having predetermined radius r on the sectional bloodstream image. As shown in FIG. 17A, CPU 12 makes imaginary point P1 where the imaginary circle and tangent line from OP to the imaginary circle contact and imaginary point P2 which is diametrically opposite to P1 on the imaginary circle. CPU 12 stores bloodstream associated value on each imaginary point P2 of the imaginary circle on the memory 20 when the radius r of the imaginary circle is varied from the length of 1 pixel to 12 pixels by 0.5 pixel step. FIG. 17B shows a graph plotting the bloodstream associated value on the imaginary point P2 at each radius r. In this graph, horizontal axis denotes the radius r and r=0 is positioned at the center. To the left and right sides from the center, r is increased. The graph shows bloodstream associated value becomes maximum when the radius r is 0. Increasing r makes bloodstream associated value on the imaginary point P2 reduced toward minimum bloodstream associated value which corresponds to lateral ventricular (LV).

CPU 12 decides radius r which corresponds border of thalamus at which the bloodstream associated value on the imaginary point P2 shows 70% of the maximum bloodstream associated value where the minimum bloodstream associated value is set as 0% (see FIG. 17). Then, CPU 12 identifies the imaginary point P1 on the imaginary circle having the decided radius r as the subthalamic point (TH). CPU 12 also decides the subthalamic point (TH) based on the other sectional bloodstream images. CPU 12 calculates mean of y coordinate values and mean of z coordinate values of all the decided subthalamic points (THs). CPU 12 decides the position of the subthalamic point (TH) based on the mean of y coordinate values and mean of z coordinate values on the interhemispheric mid-sagittal plane (see FIG. 16B).

Figure 16D:
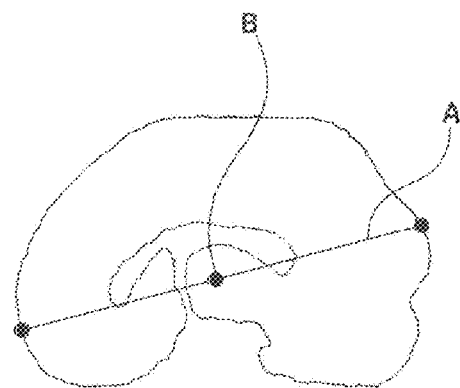

CPU 12 generates regression line connecting through the occipital pole point (OP), the subthalamic point (TH), the inferior aspect of the anterior corps callosum (CC) and the frontal pole point (FP) on the interhemispheric mid-sagittal plane. CPU 12 identifies the generated regression line as the AC-PC line A (step S237). Then, center point B of the AC-PC line A is decided as a point which possesses half length of the AC-PC line as shown in FIG. 16D (step S238). Identifying the AC-PC line and the center thereof is disclosed in Minoshima et al., "An Automated Detection of the Intercommissural Line for Stereotactic Localization of Functional Brain Images" J Nucl Med 1993; 34: 322-329, which is expressly incorporated herein by reference.

3.2.3 Positioning Subject's Image to Normal Brain

Once the AC-PC line and the center thereof are identified, CPU 12 positions the normalized 3-D bloodstream image of each subject to the standard brain image data 28 recorded in the hard-disk 14 by superposing the AC-PC lines and the centers of both images (step S24 of FIG. 10). Direction of subject's normalized 3-D bloodstream image is aligned to that of the standard brain image by matching the AC-PC line of the subject's normalized 3-D bloodstream image to that of the standard brain image. Position of subject's normalized 3-D bloodstream image is aligned to that of the standard brain image in the anteroposterior direction by matching the center of the AC-PC line to that of the standard brain image.

In this embodiment, $^{18}$F-FDG PET image is used as the standard brain image. The standard image is made by transforming the images of a number of normal subjects in accordance with the standard brain shape and averaging them. The standard brain image of $^{18}$F-FDG PET is well-used and easily obtainable.

3.2.4 Linearly Transforming Subject's Image

After positioning the subject's normalized 3-D bloodstream image to the normal brain, CPU 12 linearly transforms the subject's normalized 3-D bloodstream image in accordance with the standard brain image by the following steps.

First, CPU 12 provides Y-axis which is the AC-PC line of the subject's normalized 3-D bloodstream image, Z-axis which is the line on the interhemispheric mid-sagittal plane which passes through the center of the AC-PC line and is perpendicular to the AC-PC line and X-axis which is the normal line of the interhemispheric mid-sagittal plane which passes through the center of the AC-PC line. The center of the AC-PC line is, therefore, provided as the original point of the coordinate system. Then, CPU 12 obtains Y coordinate positions of the most anterior and the posterior points, Z coordinate positions of the most upper and the lowest points and X coordinate positions of the right most and the left most points of the subject's normalized 3-D bloodstream image. CPU 12 also obtains the Y coordinate positions, the z coordinate positions and the X coordinate positions of the standard brain image which may be previously obtained and stored.

CPU 12 transforms the subject's normalized 3-D bloodstream image so that the outer border of the subject's bloodstream image is adjusted to the outer border of the standard brain image by using the obtained X, Y and Z coordinate positions of the subject's normalized 3-D bloodstream image and shoes of the standard brain image (step S25 of FIG. 10).

Figure 18:
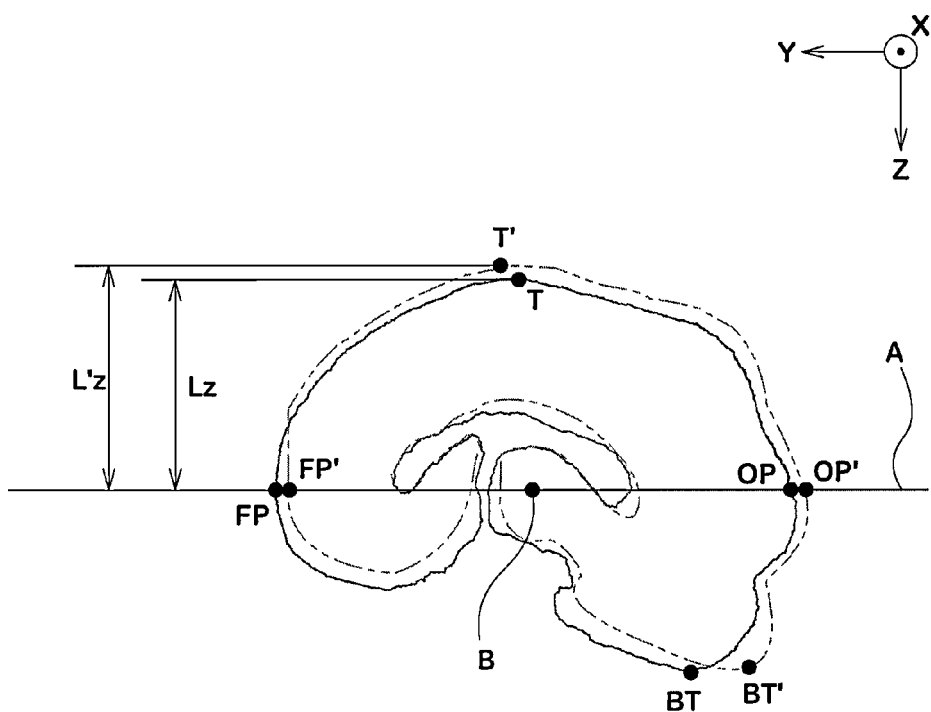
FIG. 18 shows liner transformation of the bloodstream image to adjust the bloodstream image with the anatomical standard brain.

Referring to FIG. 18, for example, the subject's normalized 3-D bloodstream image (shown by solid line) is superposed on the standard brain image (shown by chained line). CPU 12 finds the most upper point T of the outer border of the subject's normalized 3-D bloodstream image and obtains Z coordinate value Lz of the point T. CPU 12 also finds the most upper point T' of the outer border of the standard brain image and obtains Z coordinate value L'z of the point T'. Then, CPU 12 transforms Z coordinate values of the subject's normalized 3-D bloodstream image by the following equation:

$$Z'=Z(Lz/L'z)$$

where Z' is the transformed Z coordinate value of the subject's normalized 3-D bloodstream image, Z is the original Z coordinate value of the subject's normalized 3-D bloodstream image, Lz is the Z coordinate value of the point T and L'z is the Z coordinate value of the point T'.

By the transformation, the subject's normalized 3-D bloodstream image is adjusted to the standard brain image with respect to upper direction.

CPU 12 also transforms the subject's normalized 3-D bloodstream image with respect to lower, right, left, anterior and posterior direction by the same way as that of the upper direction.

3.2.5 Non-Linearly Transforming Subject's Image

Although the subject's normalized 3-D bloodstream image is aligned in accordance with the standard brain image by the liner transforming, some misalignments between the both images still remain. CPU 12 partially transforms the subject's normalized 3-D bloodstream image based on profile curve of the bloodstream associated value of the subject's normalized 3-D bloodstream image and profile curve of the glucose metabolism of the standard brain image (step S26).

Figure 19A:
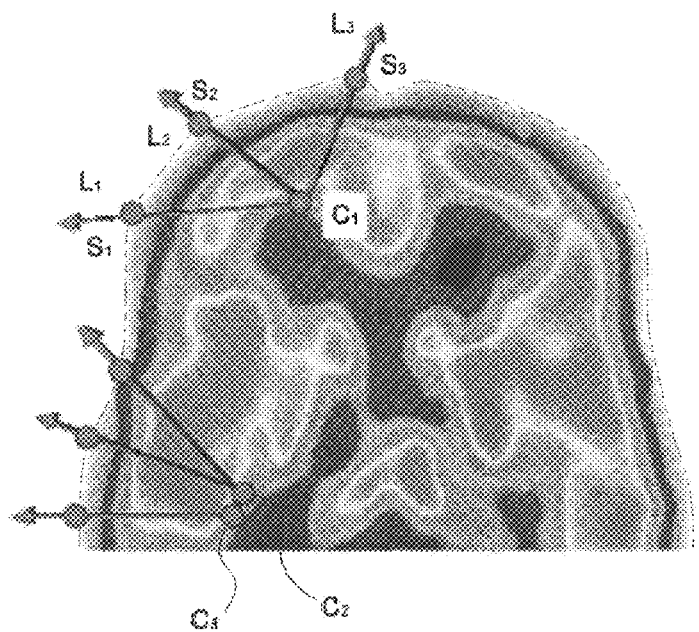
FIG. 19 shows non-liner transformation of the bloodstream image in accordance with the anatomical standard brain.
Figure 19B:
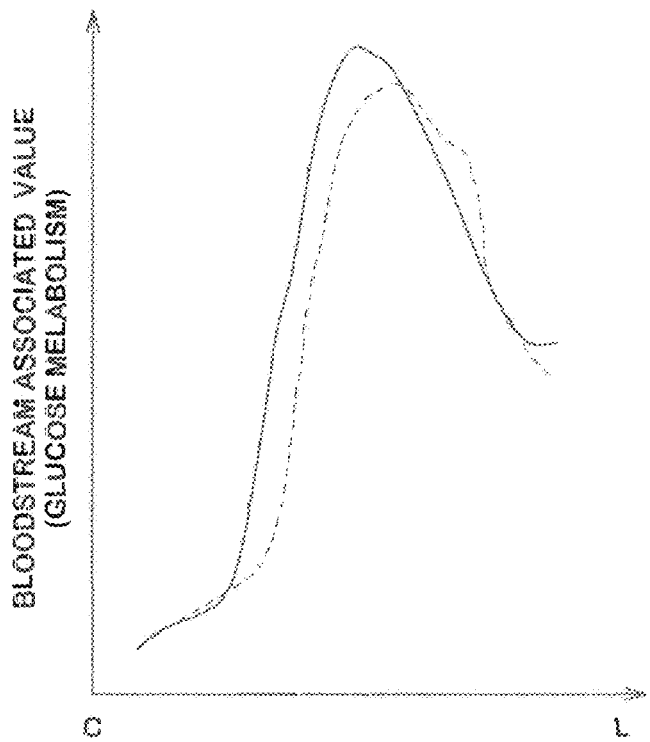

Referring to FIG. 19A, plural landmarks C1, C2 . . . Cn on white matter are predetermined in the standard brain image. Plural landmarks S1, S2 . . . Sn on brain surface are also predetermined corresponding to the landmarks C1, C2 . . . Cn in the standard brain image. In FIG. 19A, the landmarks S1, S2 and S3 of brain surface are provided corresponding to the landmarks C1 of white matter. CPU 12 generates the profile curve of the bloodstream associated values by obtaining the bloodstream associated values on the subject's normalized 3-D bloodstream image along a line L1 connecting the landmarks from C1 to S1 (see solid curve of FIG. 19B). CPU 12 obtains the profile curve of glucose metabolism on the standard brain image along the line L1 (see chained curve of FIG. 19B). In this embodiment, the profile curve of glucose metabolism on the standard brain image is prerecorded in the hard-disk 14.

CPU 12 partially transforms the subject's normalized 3-D bloodstream image so that the profile curve of the bloodstream associated values of the subject's normalized 3-D bloodstream image accords to the profile curve of the glucose metabolism values at each corresponding point, because the profile curve of the glucose metabolism values is well matched with that of the bloodstream associated values. The partial transformation (non-liner transformation) is carried out along the direction of line L1 and the landmark C1 is fixed. With regard to the line L2 between the landmarks C1 and S2 and the line L3 between the landmarks C1 and S3, CPU 12 also transforms the subject's normalized 3-D bloodstream image by same way. In area between the lines L1 and L2 (L2 and L3), CPU 12 transforms these areas based on the transforming rates on L1 and L2 (L2 and L3). The non-liner transformation is carried out with regard to each line L connecting each landmark C of white matter and corresponding landmark S of brain surface. Although in the above description, non-linear transformation is described on two-dimensional model, the non-linear transformation is carried out in three-dimensional space in this embodiment.

The liner and non-liner transforming is disclosed in Minoshima et. al. "An Anatomic Standardization: Liner Scaling and Nonliner Warping of Functional Brain Images" J Nucl Med 1994; 35: 1528-1537, which is expressly incorporated by reference herein.

3.2.6 Generating Brain Surface Bloodstream Image

Figure 20:
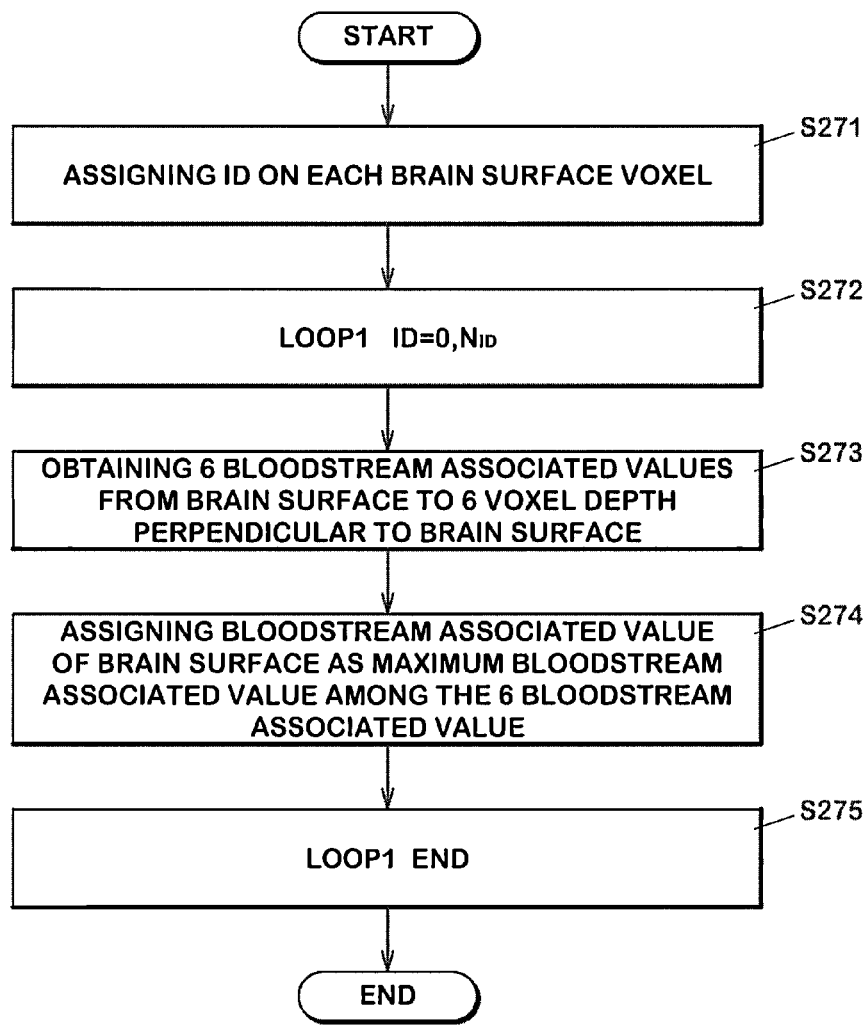
FIG. 20 shows a detailed flowchart for generating the brain bloodstream image (step S27 of FIG. 11).

After anatomically transforming the subject's transformed 3-D bloodstream image, CPU 12 generates the brain surface bloodstream image (step S27 of FIG. 11). FIG. 20 shows detailed flowchart for generating the brain surface bloodstream image.

CPU 12 identifies each brain surface voxel positioned at the most outer surface of the subject's normalized 3-D bloodstream image and assigns identification number for each identified surface voxel (step S271). In this embodiment, approximate 20,000 surface voxels are identified.

CPU 12 carries out the following steps for each identified surface voxel:

CPU 12 obtains bloodstream associated values of several number ("6" in this embodiment) of voxels from the brain surface to predetermined depth perpendicular to the brain surface in the subject's transformed 3-D bloodstream image (step S273). Then, CPU 12 selects the maximum bloodstream associated value among the several numbers of voxels as representative bloodstream associated value and the selected maximum bloodstream associated value is assigned to the brain surface voxel (step S274).

CPU 12 carries out such process for each brain surface voxel. Then, brain surface bloodstream image in which the representative bloodstream associated value is indicated at each surface voxel is obtained.

CPU 12 stores the brain bloodstream images generated in step S26 and the brain surface bloodstream images generated in step S27 on the hard-disk 14 (step S28 of FIG. 11).

When next subject's unprocessed bloodstream image exists, CPU 12 reads out the next subject's unprocessed bloodstream image from the hard-disk 14 (step S30) and carries out the process described above (following steps of step S22 of FIG. 10). When all subject's bloodstream images are processed (step S29), CPU 12 finishes the anatomical standardization (step S2 of FIG. 6).

3.3 Generating Alternative Normal Brain Database

After generating anatomically standardized subject's brain bloodstream image and brain surface bloodstream image, CPU 12 generates alternative normal brain database (step S3 of FIG. 6). When all subjects are normal healthy, the alternative normal brain database can be simply obtained by calculating mean value and standard deviation of each point of the brain bloodstream images and brain surface bloodstream images of anatomically standardized. However, the subjects contain patient(s) in this embodiment. Therefore, the alternative normal brain database is generated in this embodiment after rejecting bloodstream associated values regarded as disease part.

Figure 21:
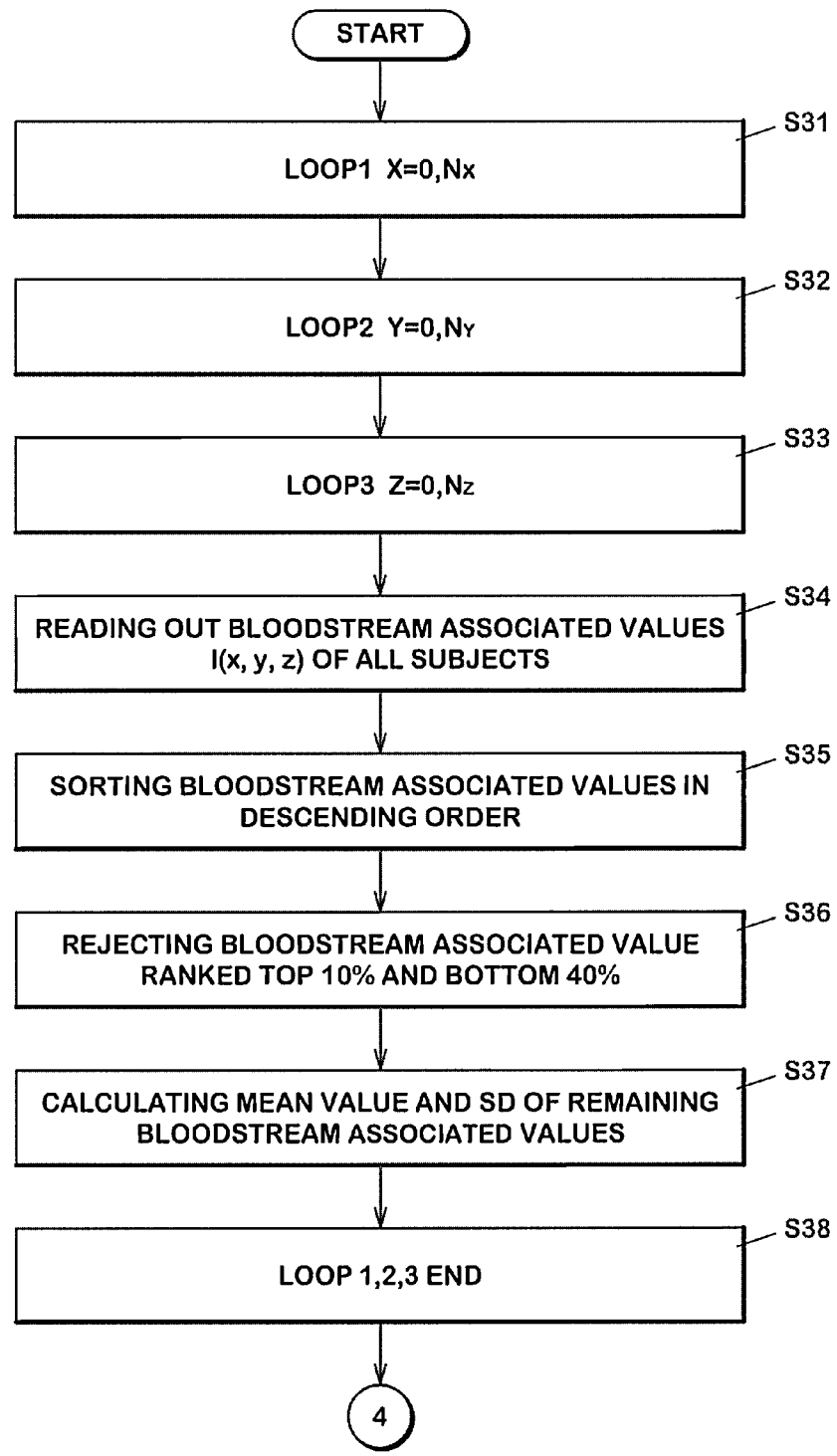
FIG. 21 shows a detailed flowchart for generating the alternative normal brain database (step S3 of FIG. 6).
Figure 22:
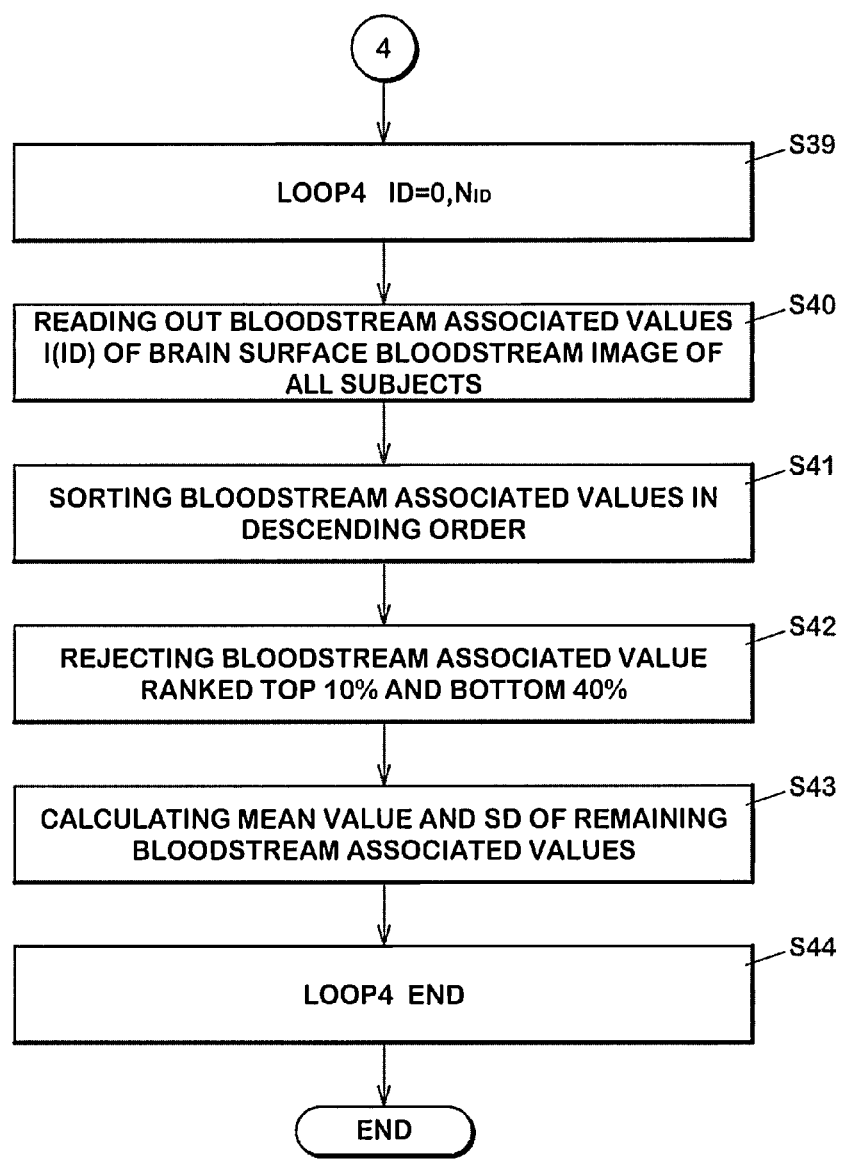
FIG. 22 shows a detailed flowchart for generating the alternative normal brain database (step S3 of FIG. 6).

FIGS. 21 and 22 show detailed flowchart for generating the alternative normal brain database. CPU 12 reads out the normalized bloodstream associated values of target voxel of all subject's standardized brain bloodstream images (step S34). Then, CPU 12 sorts the bloodstream associated values in descending order (step S35). FIG. 23 shows sorted bloodstream associated values of the target voxel. In FIG. 23, the bloodstream associated values of subjects at target voxel (positioned at x=11, y=25 and z=135) are shown in the descending order. Subject ID means identification of subject which is assigned to each subject uniquely.

CPU 12 rejects bloodstream associated values that are ranked in the top 10% and in the bottom 40% (step S36). The percentage of the rejecting may be selected arbitrarily. When the number of the subjects are 20 for example, bloodstream associated values of the highest 2 subjects and of the lowest 8 subjects are rejected. In this embodiment, bottom values are rejected, because a part having reduced bloodstream associated value is regarded as corresponding to disease part such as Alzheimer's disease. Higher values are also rejected, because it sometimes occurs that even the bloodstream associated value of the part except the disease part vary widely from those of the normal healthy subjects due to the influence of the normalization (step S13 of FIG. 7). Because the lower values are regarded as corresponding to the disease part, rejected percentages of the lower values are higher than that of the higher values in this embodiment.

Then, CPU 12 calculates and stores mean value and standard deviation of remaining bloodstream associated values after the rejection (step S37). As described above, mean value and standard deviation of the bloodstream associated values at target voxel (11, 25, 135) are calculated and stored on the hard-disk 14 (see FIG. 24).

Figure 24:
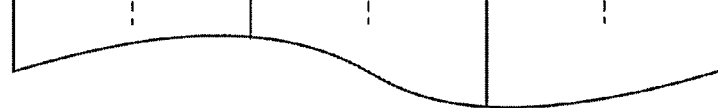
FIG. 24 shows a part of the generated alternative normal brain database of brain bloodstream.

CPU 12 calculates mean value and standard deviation of bloodstream associated values for each voxel as target voxel (steps S31, S32, S33 and S38). Then, the alternative normal brain database of brain bloodstream image is obtained as shown in FIG. 24.

Next, CPU 12 calculates mean value and standard deviation of bloodstream associated values with regard to the patient's brain surface bloodstream images. CPU 12 reads out the bloodstream associated values of target surface voxel of all the subject's standardized brain bloodstream images (step S40). Then, CPU 12 sorts the bloodstream associated values in descending order (step S41).

CPU 12 rejects bloodstream associated values that are ranked in the top 10% and in the bottom 40% (step S42). When the number of the subjects are 20 for example, bloodstream associated values of the highest 2 subjects and of the lowest 8 subjects are rejected.

Figure 25:
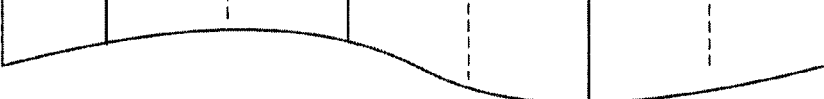
FIG. 25 shows a part of the generated alternative normal brain database of brain surface bloodstream.

Then, CPU 12 calculates and stores mean value and standard deviation of remaining bloodstream associated values after the rejection (step S43). The alternative normal brain database of brain surface bloodstream image is obtained as shown in FIG. 25.

4. Other Embodiments

Identifying interhemispheric mid-sagittal plane and PC-AC line and positioning AC-PC line shown as steps S22, S23 and S24 of FIG. 10 may be substituted by aligning method using mutual information in which the subject's bloodstream image is moved against the standard brain image in dribs and mutual information between the both images is used to find the best aligning position. The aligning method using mutual information is disclosed in F. Maes et al., "Multimodality Image Registration by Maximization of Mutual Information," IEEE Transactions on Medical Imaging, (USA), 1997, 16, 2, p 187-198, which is expressly incorporated herein by reference. The aligning method using mutual information can be achieved by the stereo program contained in 3D-SSP program (provided by Satoshi Minoshima, Professor of University of Washington).

Although the bloodstream associated values regarded as outlier due to the normalization are rejected in addition to the bloodstream associated values regarded as brain disease part in the above mentioned embodiment. However, only one of the bloodstream associated values regarded as outlier due to the normalization or the bloodstream associated values regarded as brain disease part may be rejected.

It is suitable to assume the bloodstream associated values indicating disease part and reject the predetermined percentage of the lower bloodstream associated values as described in the above mentioned embodiment when the number of subjects is large and the predetermined percentage can be accurately predicted, because the rejection can be carried out by simple calculation.

Instead of the above mentioned rejection method, following statistical rejection methods may be used. For example, THOMPSON's method (William R. Thompson, The annals of Mathematical Statistics, Vol 6, No. 4 (December 1935), pp 214-219), SMIRNOV-GRUBBS's method (Frank E. Grubbs, The annals of Mathematical Statistics, Vol 21, No. 1 (March, 1950), pp. 27-58) may be used.

Figure 26:
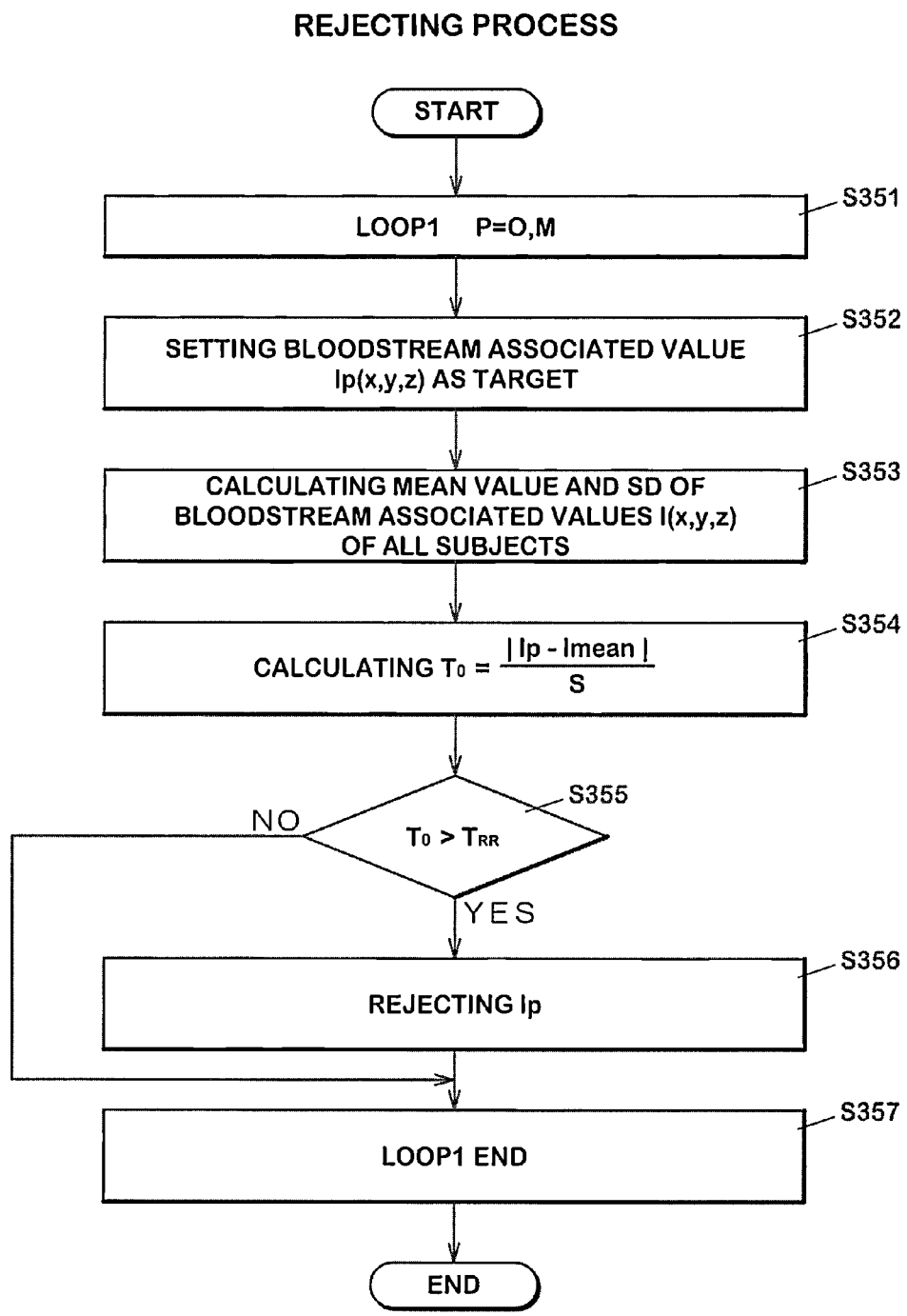
FIG. 26 shows a detailed flowchart of rejecting process in another embodiment.

When using THOMPSON's method, steps S35 and S36 of FIG. 21 are substituted for steps shown in FIG. 26.

Referring to FIG. 26, CPU 12 sets a bloodstream associated value Ip (x, y, z) of a subject as target subject's bloodstream associated value (step S352). CPU 12 calculates mean value $I_{mean}$ (x, y, z) and standard deviation SD (x, y, z) of bloodstream associated values of all subjects (step S353).

Then, CPU 12 calculates index $T_0$ according to following equation (step S354):

$$T_0 = (Ip(x,y,z) - I_{mean}(x,y,z))/SD(x,y,z)$$

CPU 12 compares the index $T_0$ and limit Ta (step S355). The limit Ta is decided by combination of risk rate RR and the number of subjects M. In this embodiment, CPU 12 obtains the limit Ta according to a table (per-recorded on the hard-disk 14) as shown in FIG. 27. The risk rate RR is a factor indicating rate of rejection and more bloodstream associated values are rejected when the risk rate RR grows higher. When the number M of subject is 20 and the risk rate RR is 5%, the limit Ta is decided as 1.93 from the table of FIG. 27.

CPU 12 rejects the target subject's bloodstream associated value Ip (x, y, z) when the index $T_0$ is larger than the limit Ta (step S35) and does not reject the target subject's bloodstream associated value Ip (x, y, z) when the index $T_0$ is not larger than the limit Ta.

CPU 12 repeatedly carries out the above mentioned process for each subject's bloodstream associated value as the target bloodstream associated value (steps S351 and S357).

In the embodiment shown in FIG. 26, the same risk rate RR is used for both the upper side and the lower side outlier. However, the risk rate RR of one side on which the disease affects the bloodstream (for example, lower bloodstream associated value side) may be higher than that of the other side on which the disease does not affect the bloodstream (for example, higher bloodstream associated value side). Instead, the rejection process may be carried out only for the one side in which the disease affects the bloodstream.

As shown in the table of FIG. 27, the number of subjects should be more than 3 for rejecting process. In order to secure the degrees of freedom, it is necessary to have predetermined number of subjects for the statistical rejecting process such as Thompson's method.

Although in the above mentioned embodiments, brain bloodstream image obtained by SPECT and PET etc. is used, other functional images may be used.

Although in the above mentioned embodiments, normalization of status values (bloodstream associated values) is carried out before the spatial transformation, the normalization may be carried out after the spatial transformation or the normalization and the spatial transformation may be carried out simultaneously.

While the embodiments of the present invention disclosed herein are presently considered to be preferred embodiments, various changes and modifications can be made without departing from the spirit and scope of the present invention. The scope of the invention is indicated in the appended claims, and all changes that come within the meaning and range of equivalents are intended to be embraced therein.

DRAWINGS

Figure 1:
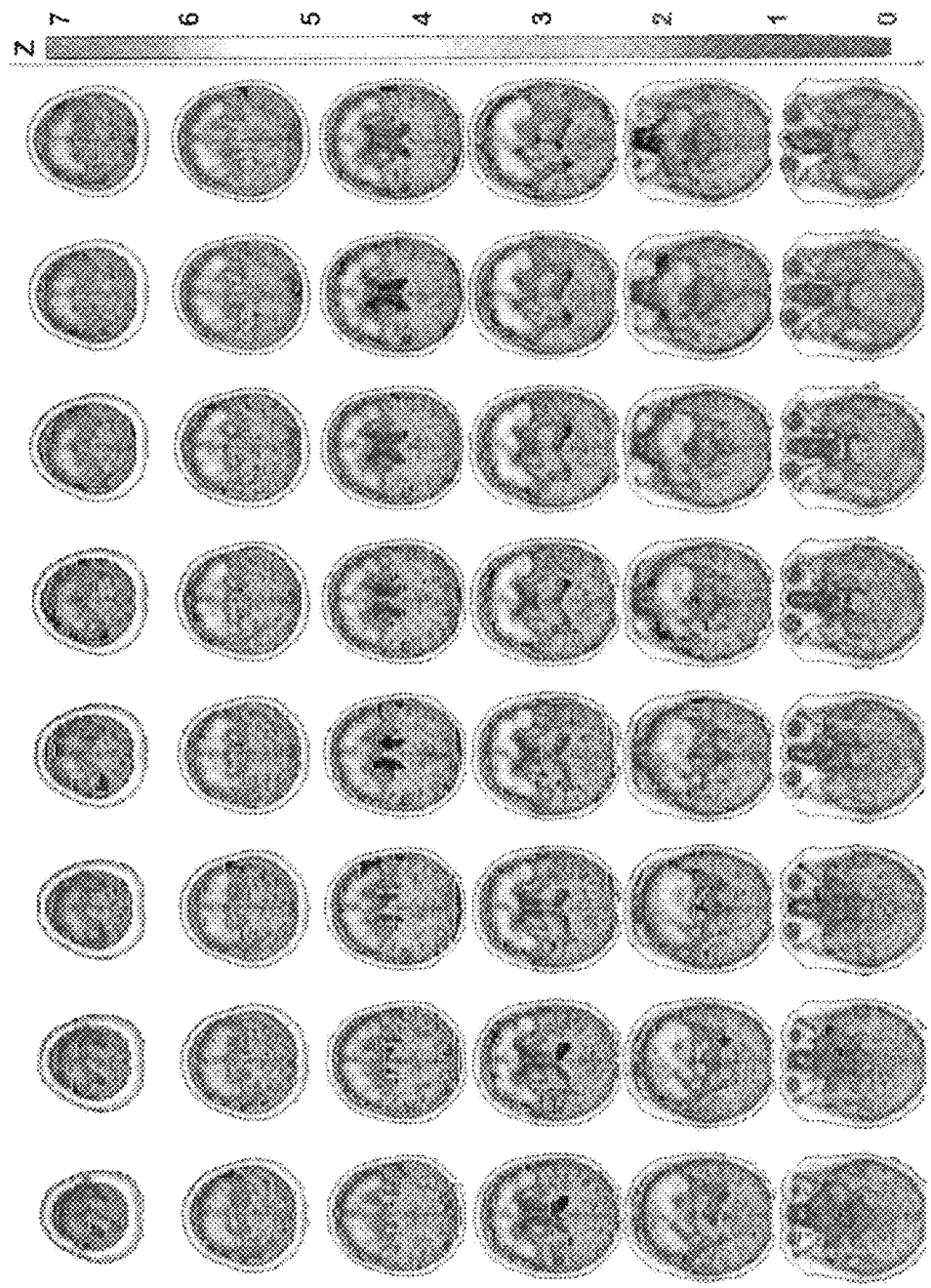
FIG. 1 shows plural sectional images of brain bloodstream associated value.
Figure 2:
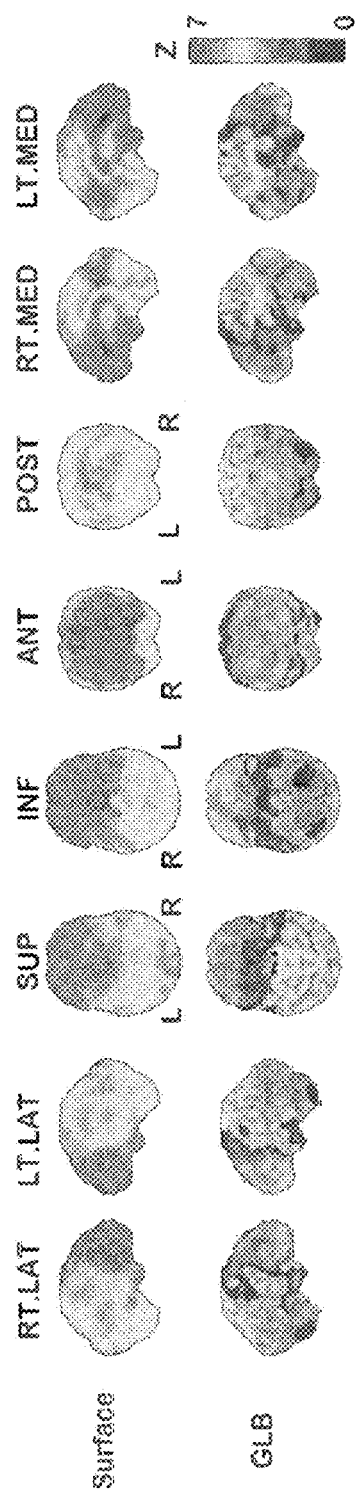
FIG. 2 shows images of brain surface bloodstream associated value.

[FIG. 1]
[FIG. 2]
[FIG. 3]
[FIG. 4]
[FIG. 5]
[FIG. 6]
[FIG. 7]
[FIG. 8]
[FIG. 9]
[FIG. 10]
[FIG. 11]
[FIG. 12]
[FIG. 13]
[FIG. 14]
[FIG. 15]
[FIG. 16]
[FIG. 17]
[FIG. 18]
[FIG. 19]
[FIG. 20]
[FIG. 21]
[FIG. 22]
[FIG. 23]
[FIG. 24]
[FIG. 25]
[FIG. 26]
[FIG. 27]

The invention claimed is:

1. A device for generating alternative of normal brain database to be used for diagnosing brain disease based on brain status images of subjects including patients, the alternative of normal brain database showing normal status of each points of brain, the device comprising:
    means for normalizing status value at each point of each brain status image of subject based on status values of a part or whole of brain status image of the subject;
    means for spatially transforming each brain status image of subject in accordance with anatomical standard brain;
    means for rejecting status values presumed as indicating disease with regard to each points of brain to be used for diagnosing disease based on said anatomically transformed and normalized brain status images of subjects; and
    means for generating the alternative of normal brain database by obtaining at least mean status value for said each point of brain to be used for diagnosing disease based on said anatomically transformed and normalized brain status images of subjects in which said status values presumed as indicating disease are rejected.

2. A device for generating alternative of normal brain database in accordance with claim 1, wherein
    said rejecting means rejects extreme deviate values statistically obtained at each point as said status values presumed as indicating disease.

3. A device for generating alternative of normal brain database in accordance with claim 2, wherein
    said brain status image is a brain bloodstream image which shows bloodstream associated value of each points of brain.

4. A device for generating alternative of normal brain database in accordance with claim 3, wherein
    said rejecting means rejects the smallest value to the m-th smallest as said status values presumed as indicating disease for each points of brain to be used for diagnosing disease based on anatomically transformed and normalized brain status images of subjects.

5. A device for generating alternative of normal brain database in accordance with claim 4, wherein
    said rejecting means further rejects the largest value to the n-th largest for each points of brain to be used for diagnosing disease based on anatomically transformed and normalized brain status images of subjects.

6. A device for generating alternative of normal brain database in accordance with claim 5, wherein
the number m of rejecting the smallest value to the m-th smallest is larger than the number n of rejecting the largest value to the n-th largest.

7. A device for generating alternative of normal brain database in accordance with claim 1, wherein
said generating means generates the alternative of normal brain database by obtaining mean status value and standard deviation for said each point of brain to be used for diagnosing disease based on said anatomically transformed and normalized brain status images of subjects in which said status values presumed as indicating disease are rejected.

8. A device for generating alternative of normal brain database in accordance with claim 1, further comprising:
means for generating brain surface status image of each subject based on said anatomically transformed and normalized brain status images of subjects, said brain surface status image having surface status value of each surface portion, said surface status value being selected as representative value of status values from brain surface to predetermined depth perpendicular to the brain surface; and
wherein said each surface point at which said surface status value is indicated is used as said point of brain to be used for diagnosing disease.

9. A device for generating alternative of normal brain surface database to be used for diagnosing disease, based on brain bloodstream images of subjects including patients which show bloodstream associated value of each points of brain, the device comprising:
means for normalizing bloodstream associated value at each point of each brain bloodstream image of subject based on bloodstream associated values of a part or whole of brain bloodstream image of the subject;
means for spatially transforming each brain bloodstream image of subject in accordance with anatomical standard brain;
means for generating brain surface bloodstream image of each subjects based on said anatomically transformed and normalized brain bloodstream images of subjects, said brain surface bloodstream image having surface bloodstream associated value of each surface points, said surface bloodstream associated value being selected as representative value of bloodstream associated values from brain surface to predetermined depth perpendicular to the brain surface; and
means for generating the alternative of normal brain surface database by obtaining mean bloodstream associated value and standard deviation for each surface points based on generated brain surface bloodstream image of each subjects, said mean bloodstream associated value and standard deviation being obtained by calculating average of selected bloodstream associated values and standard deviations of the surface portion, said selected bloodstream associated values are selected from all bloodstream associated values of the surface portion by excluding at least the smallest value to m-th smallest.

10. A non-transitory computer-readable recording medium storing program for generating alternative of normal brain database to be used for diagnosing brain disease based on brain status images of subjects including patients, the alternative of normal brain database showing normal status of each points of brain, the program comprising instructions for the steps of: normalizing status value at each point of each brain status image of subject based on status values of a part or whole of brain status image of the subject; spatially transforming each brain status image of subject in accordance with anatomical standard brain; rejecting status values presumed as indicating disease with regard to each points of brain to be used for diagnosing disease based on said anatomically transformed and normalized brain status images of subjects; and
generating the alternative of normal brain database by obtaining at least mean status value for said each point of brain to be used for diagnosing disease based on said anatomically transformed and normalized brain status images of subjects in which said status values presumed as indicating disease are rejected.

11. A non-transitory computer-readable recording medium storing program for generating alternative of normal brain database in accordance with claim 10, wherein
said rejected status values in said rejecting step are extreme deviate values statistically obtained at each point as said status values presumed as indicating disease.

12. A non-transitory computer-readable recording medium storing program for generating alternative of normal brain database in accordance with claim 11, wherein
said brain status image is a brain bloodstream image which shows bloodstream associated value of each points of brain.

13. A non-transitory computer-readable recording medium storing program for generating alternative of normal brain database in accordance with claim 12, wherein
said rejected status values in said rejecting step are the smallest value to the m-th smallest as said status values presumed as indicating disease for each points of brain to be used for diagnosing disease based on anatomically transformed and normalized brain status images of subjects.

14. A non-transitory computer-readable recording medium storing program for generating alternative of normal brain database in accordance with claim 13, wherein
the largest value to the n-th largest for each points of brain to be used for diagnosing disease based on anatomically transformed and normalized brain status images of subjects are further rejected in said rejecting step.

15. A non-transitory computer-readable recording medium storing program for
generating alternative of normal brain database in accordance with claim 14, wherein
the number m of rejecting the smallest value to the m-th smallest is larger than the number n of rejecting the largest value to the n-th largest.

16. A non-transitory computer-readable recording medium storing program for generating alternative of normal brain database in accordance with claim 10, wherein
in said generating step the alternative of normal brain database is generated by obtaining mean status value and standard deviation for said each point of brain to be used for diagnosing disease based on said anatomically transformed and normalized brain status images of subjects in which said status values presumed as indicating disease are rejected.

17. A non-transitory computer-readable recording medium storing program for generating alternative of normal brain database in accordance with claim 10, further comprising instruction for the step of:
generating brain surface status image of each subject based on said anatomically transformed and normalized brain status images of subjects, said brain surface status image having surface status value of each surface portions, said surface status value being selected as representative value of status values from brain surface to predetermined depth perpendicular to the brain surface; and wherein said each surface point at which said surface status value is indicated is used as said point of brain to be used for diagnosing disease.

18. A non-transitory computer-readable recording medium storing program for generating alternative of normal brain surface database to be used for diagnosing disease, based on brain bloodstream images of subjects including patients which show bloodstream associated value of each points of brain, the program comprising instructions for the steps of:

normalizing bloodstream associated value at each point of each brain bloodstream image of subject based on bloodstream associated values of a part or whole of brain bloodstream image of the subject;

spatially transforming each brain bloodstream image of subject in accordance with anatomical standard brain;

generating brain surface bloodstream image of each subjects based on said anatomically transformed and normalized brain bloodstream images of subjects, said brain surface bloodstream image having surface bloodstream associated value of each surface points, said surface bloodstream associated value being selected as representative value of bloodstream associated values from brain surface to predetermined depth perpendicular to the brain surface; and generating the alternative of normal brain surface database by obtaining mean bloodstream associated value and standard deviation for each surface points based on generated brain surface bloodstream image of each subjects, said mean bloodstream associated value and standard deviation being obtained by calculating average of selected bloodstream associated values and standard deviations of the surface portion, said selected bloodstream associated values are selected from all bloodstream associated values of the surface portion by excluding at least the smallest value to m-th smallest.

19. A method for generating alternative of normal brain database to be used for diagnosing brain disease based on brain status images of subjects including patients, the alternative of normal brain database showing normal status of each points of brain, the method comprising the steps of:

normalizing status value at each point of each brain status image of subject based on status values of a part or whole of brain status image of the subject;

spatially transforming each brain status image of subject in accordance with anatomical standard brain;

rejecting status values presumed as indicating disease with regard to each points of brain to be used for diagnosing disease based on said anatomically transformed and normalized brain status images of subjects; and generating the alternative of normal brain database by obtaining at least mean status value for said each point of brain to be used for diagnosing disease based on said anatomically transformed and normalized brain status images of subjects in which said status values presumed as indicating disease are rejected.

20. A method for generating alternative of normal brain database in accordance with claim 19, wherein said rejected status values in said rejecting step are extreme deviate values statistically obtained at each point as said status values presumed as indicating disease.

21. A method for generating alternative of normal brain database in accordance with claim 20, wherein said brain status image is a brain bloodstream image which shows bloodstream associated value of each points of brain.

22. A method for generating alternative of normal brain database in accordance with claim 21, wherein said rejected status values in said rejecting step are the smallest value to the m-th smallest as said status values presumed as indicating disease for each points of brain to be used for diagnosing disease based on anatomically transformed and normalized brain status images of subjects.

23. A method for generating alternative of normal brain database in accordance with claim 22, wherein the largest value to the n-th largest for each points of brain to be used for diagnosing disease based on anatomically transformed and normalized brain status images of subjects are further rejected in said rejecting step.

24. A method for generating alternative of normal brain database in accordance with claim 23, wherein the number m of rejecting the smallest value to the m-th smallest is larger than the number n of rejecting the largest value to the n-th largest.

25. A method for generating alternative of normal brain database in accordance with claim 19, wherein in said generating step the alternative of normal brain database is generated by obtaining mean status value and standard deviation for said each point of brain to be used for diagnosing disease based on said anatomically transformed and normalized brain status images of subjects in which said status values presumed as indicating disease are rejected.

26. A method for generating alternative of normal brain database in accordance with claim 19, further comprising the step of:

generating brain surface status image of each subject based on said anatomically transformed and normalized brain status images of subjects, said brain surface status image having surface status value of each surface portions, said surface status value being selected as representative value of status values from brain surface to predetermined depth perpendicular to the brain surface; and wherein said each surface point at which said surface status value is indicated is used as said point of brain to be used for diagnosing disease.

27. A method for generating alternative of normal brain surface database to be used for diagnosing disease, based on brain bloodstream images of subjects including patients which show bloodstream associated value of each points of brain, the method comprising the steps of:

normalizing bloodstream associated value at each point of each brain bloodstream image of subject based on bloodstream associated values of a part or whole of brain bloodstream image of the subject;

spatially transforming each brain bloodstream image of subject in accordance with anatomical standard brain;

generating brain surface bloodstream image of each subjects based on said anatomically transformed and normalized brain bloodstream images of subjects, said brain surface bloodstream image having surface bloodstream associated value of each surface points, said surface bloodstream associated value being selected as representative value of bloodstream associated values from brain surface to predetermined depth perpendicular to the brain surface; and generating the alternative of normal brain surface database by obtaining mean bloodstream associated value and standard deviation for each surface points based on generated brain surface bloodstream image of each subjects, said mean bloodstream associated value and standard deviation being obtained by calculating average of selected bloodstream associated values and standard deviations of the surface portion, said selected bloodstream associated values are selected from all bloodstream associated values of the surface portion by excluding at least the smallest value to m-th smallest.

\* \* \* \* \*

UNITED STATES PATENT AND TRADEMARK OFFICE
CERTIFICATE OF CORRECTION

PATENT NO. : 8,472,694 B2 Page 1 of 1
APPLICATION NO. : 13/120053
DATED : June 25, 2013
INVENTOR(S) : Satoshi Minoshima et al.

It is certified that error appears in the above-identified patent and that said Letters Patent is hereby corrected as shown below:

On the Title page, immediately following item (65), column 1, beginning at line 24, please insert the following:

--(30)    Foreign Application Priority Data
    Sep. 22, 2008  (US).............................12/234,910--

Signed and Sealed this
Thirtieth Day of July, 2013

Teresa Stanek Rea
*Acting Director of the United States Patent and Trademark Office*